(12) United States Patent
Maeno et al.

(10) Patent No.: US 6,245,796 B1
(45) Date of Patent: Jun. 12, 2001

(54) TRICYCLIC PYRROLE OR PYRAZOLE DERIVATIVE

(75) Inventors: Kyoichi Maeno; Ken-ichi Kazuta; Hideki Kubota; Itsuro Shimada; Tetsuya Kimizuka; Shuichi Sakamoto; Fumikazu Wanibuchi, all of Ibaraki (JP)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/445,104

(22) PCT Filed: Jun. 11, 1998

(86) PCT No.: PCT/JP98/02579

§ 371 Date: Dec. 2, 1999

§ 102(e) Date: Dec. 2, 1999

(87) PCT Pub. No.: WO98/56768

PCT Pub. Date: Dec. 17, 1998

(30) Foreign Application Priority Data

Jun. 13, 1997 (JP) .................................................... 9-157255

(51) Int. Cl.$^7$ .................................................... A01N 43/56
(52) U.S. Cl. ............................. 514/403; 546/82; 546/199; 548/151; 548/218; 548/242; 548/257; 548/302.1; 548/359.5
(58) Field of Search ................................ 548/359.5, 218; 514/403

(56) References Cited

U.S. PATENT DOCUMENTS

| 5,561,150 | 10/1996 | Wichmann . |
| 5,646,173 | 7/1997 | Bös et al. . |

FOREIGN PATENT DOCUMENTS

| 50-106958 | 8/1975 | (JP) . |
| 7-149723 | 6/1995 | (JP) . |
| 95/32967 | 12/1995 | (WO) . |

*Primary Examiner*—Robert W. Ramsuer
(74) *Attorney, Agent, or Firm*—Sughrue, Mion, Zinn, Macpeak & Seas, PLLC

(57) ABSTRACT

A tricyclic pyrrole or pyrazole derivative represented by the following general formula (I), or a pharmaceutically acceptable salt thereof, which shows strong affinity and selectivity for the 5-HT$_{2C}$ receptor and is useful for the treatment of central nervous system diseases such as sexual disorders, eating disorders, anxiety, depression and sleeping disorders.

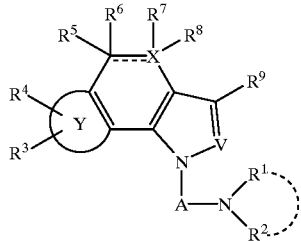

(I)

(In the above formula, each symbol means as follows;

Y ring: an unsaturated five-membered ring which may have 1 to 3 of one or more types of hetero atom(s) each selected from the group consisting of a nitrogen atom, an oxygen atom and a sulfur atom or an unsaturated six-membered ring having 1 or 2 nitrogen atom(s), X: a bond or a carbon atom, ═: a double bond or a single bond, V: a nitrogen atom or a group represented by a formula CH, and A: a straight or branched lower alkylene group which may be substituted with a halogen atom or a cycloalkyl group).

8 Claims, No Drawings

TRICYCLIC PYRROLE OR PYRAZOLE DERIVATIVE

This application is a 371 of PCT/JP98/02579 filed Jun. 11, 1998.

TECHNICAL FIELD

This invention relates to a novel tricyclic pyrrole or pyrazole derivative or a pharmaceutically acceptable salt thereof. This invention also relates to a pharmaceutical composition which comprises said tricyclic pyrrole or pyrazole derivative or a salt thereof and a pharmaceutically acceptable carrier, especially a pharmaceutical composition which is useful as a drug for the prevention and treatment of central nervous system diseases such as sexual disorders, eating disorders, anxiety, depression and sleeping disorders.

BACKGROUND ART

With the advance of aging society, improvement and betterment of living conditions for the aged have been reconsidered, so that attention has been focused on the prevention and treatment of diseases which have so far been disregarded as diseases (e.g., sexual disorders and the like).

Though the role of the 5-HT$_{2C}$ receptor which is mainly distributed in the central nerve has not been sufficiently revealed, it is considered that this receptor is related to the central nervous system diseases such as sexual disorders, eating disorders, anxiety, depression and sleeping disorders (*Curr. Opin. Invest. Drugs*, 2 (4), 317 (1993)). In consequence, it is believed that the 5-HT$_{2C}$ receptor ligand is effective for the prevention or treatment of the aforementioned diseases, particularly diseases which have so far been disregarded as diseases and have no effective therapeutic method (e.g., sexual disorders and the like).

Regarding tricyclic pyrrole or pyrazole derivatives which are 5-HT$_{2C}$ receptor ligands, a tricyclic pyrrole derivative fused with a benzene ring (EP 657426-A), a tricyclic pyrazole derivative fused with a benzene ring (EP 700905-A) and the like have been reported.

In addition, a tricyclic pyrrole or pyrazole derivative which is fused with a pyrazine ring, a pyridine ring, a thiophene ring, a furan ring or a pyrrole ring is reported as a retinoid antagonist in International Publication WO 96/13478, and a compound having a tricyclic pyrrole or pyrazole nucleus which is fused with an aromatic heterocyclic ring and also has a substituent on a carbon atom of the pyrrole or pyrazole ring in said nucleus is reported as a dopamine receptor ligand in International Publication WO 95/07893.

DISCLOSURE OF THE INVENTION

As a result of extensive studies on a unknown tricyclic pyrrole or pyrazole derivative in which an amino group is linked at the 1-position via an alkylene chain and which is fused with an unsaturated heterocyclic ring, the inventors of the present invention have found that a novel tricyclic pyrrole or pyrazole derivative was possessed of high selectivity and affinity for the 5-HT$_{2C}$ receptor and accomplished the present invention.

Accordingly, the present invention relates to a novel tricyclic pyrrole or pyrazole derivative represented by the following general formula (I) which shows high selectivity and affinity for the 5-HT$_{2C}$ receptor, or a pharmaceutically acceptable salt thereof

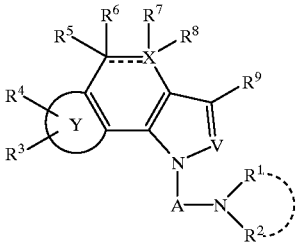

(each symbol in the above formula means as follows;

Y ring: an unsaturated five-membered ring which may have 1 to 3 of one or more types of hetero atom(s) each selected from the group consisting of a nitrogen atom, an oxygen atom and a sulfur atom or an unsaturated six-membered ring having 1 or 2 nitrogen atom(s), X: a bond or a carbon atom, ═: a double bond or a single bond, V: a nitrogen atom or a group represented by a formula CH, A: a straight or branched lower alkylene group which may be substituted with a halogen atom or a cycloalkyl group, R$^1$ and R$^2$: may be the same or different from each other and each represents a hydrogen atom or a lower alkyl group, or R$^1$ and R$^2$ or A may form a nitrogen-containing saturated heterocyclic ring together with the adjacent nitrogen atom, R$^3$ and R$^4$: may be the same or different from each other and each represents a hydrogen atom, a lower alkyl group, a hydroxyl group, a lower alkoxy group, an amino group, a mono- or di-lower alkylamino group, a lower alkanoylamino group or a halogen atom, and R$^5$ to R$^9$: may be the same or different from one another and each represents a hydrogen atom, a lower alkyl group, a hydroxyl group or a lower alkoxy group, with the proviso that, when ═ is a double bond, then R$^6$ and R$^9$ do not exist and that, when X is a bond, then ═ is a single bond and R$^7$ and R$^8$ do not exist).

The compound (I) of the present invention is characterized by its chemical structure in which an amine is linked to the 1-position of the tricyclic pyrrole or pyrazole nucleus fused with an unsaturated heterocyclic ring, always via an alkylene chain.

Among the compounds (I) of the present invention, the compounds wherein

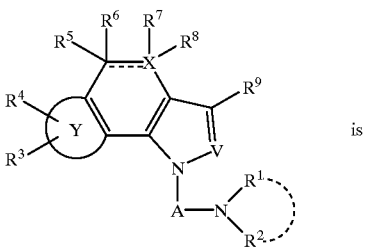 is

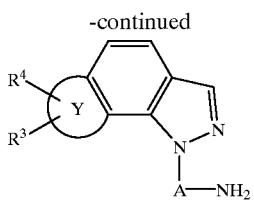

are preferable, the compounds in which A is ethylene or propylene group are more preferable, the compounds in which the Y ring is furan or thiophene are still more preferable, and 2-(1H-furo[2,3-g]indazol-1-yl)ethylamine, 2-(7-bromo-1H-thieno[2,3-g]indazol-1-yl)ethylamine, 2-(7-iodo-1H-thieno[2,3-g]indazol-1-yl)ethylamine, 2-(7-methoxy-1H-thieno[2,3-g]indazol-1-yl)ethylamine, (S)-2-(1H-furo[2,3-g]indazol-1-yl)-1-methylethylamine, 2-(7-methyl-1H-thieno[2,3-g]indazol-1-yl)ethylamine, (S)-2-(7-methoxy-1H-thieno[2,3-g]indazol-1-yl)-1-methylethylamine, (S)-1-methyl-2-(7-methyl-1H-thieno[2,3-g]indazol-1-yl)ethylamine, 2-(7-ethyl-1H-thieno[2,3-g]indazol-1-yl)ethylamine, (S)-2-(7-ethyl-1H-thieno[2,3-g]indazol-1-yl)-1-methylethylamine or a pharmaceutically acceptable salts thereof are particularly preferable.

The present invention is to provide a pharmaceutical composition which comprises a tricyclic pyrrole or pyrazole derivative represented by the general formula (I) or a pharmaceutically acceptable salt thereof and a pharmaceutically acceptable carrier, preferably a pharmaceutical composition which shows high selectivity and affinity for the $5\text{-HT}_{2C}$ receptor, more preferably a pharmaceutical composition which is a drug for the treatment of central nervous system diseases including sexual disorders such as impotence, eating disorders such as obesity, bulimia and anorexia, anxiety, depression or sleeping disorders, most preferably a pharmaceutical composition which is a drug for the treatment of sexual disorders such as impotence.

The following describes the compound (I) of the present invention in detail.

The term "$5\text{-HT}_{2C}$ receptor ligand" means a compound which has the affinity for the $5\text{-HT}_{2C}$ receptor and shows agonism or antagonism.

In the definition of the general formula as used herein, unless otherwise noted, the term "lower" means a straight or branched carbon chain having 1 to 6 carbon atoms.

Illustrative examples of the "lower alkylene group" include methylene, ethylene, trimethylene, propylene, tetramethylene, ethylethylene, pentamethylene, hexamethylene and the like, of which ethylene group and propylene group are preferred.

Illustrative examples of the "lower alkyl group" include methyl, ethyl, propyl, isopropyl, butyl, isobutyl, sec-butyl, tert-butyl, pentyl (amyl), isopentyl, neopentyl, tert-pentyl, hexyl, isohexyl and the like, of which alkyl groups having 1 to 4 carbon atoms are preferred and methyl group is particularly preferred.

The term "cycloalkyl group" means a monocyclic hydrocarbon ring group having 3 to 8 ring atoms, and its illustrative examples include cyclopropyl, cyclobutyl, cyclopentyl, cyclohexyl, cycloheptyl, cyclooctyl and the like, of which cyclohexyl group is preferred.

The term "lower alkoxy group" means an oxy group substituted with the aforementioned lower alkyl group.

The term "mono- or di-lower alkylamino group" means an amino group substituted with 1 or 2 of the aforementioned lower alkyl groups.

The term "lower alkanoylamino group" means a carbonylamino group substituted with hydrogen atom or the aforementioned lower alkyl group.

Examples of the "halogen atom" include fluorine, chlorine, bromine and iodine atoms, of which chlorine, bromine or iodine atom is preferred.

Illustrative examples of the "five-membered unsaturated ring which may have 1 to 3 of one or more types of hetero atom(s) each selected from the group consisting of a nitrogen atom, an oxygen atom and a sulfur atom" include pentene, pentadiene, thiophene, furan, pyrrole, imidazole, pyrazole, thiazole, oxazole, isothiazole, isoxazole, triazole, thiadiazole, oxadiazole and the like, of which thiophene and furan are preferred.

Illustrative examples of the "six-membered unsaturated ring having 1 or 2 nitrogen atom(s)" include pyridine, pyridazine, pyrimidine, pyrazine and the like, of which pyridine is preferred.

The term "nitrogen-containing saturated heterocyclic ring" means a three- to eight-membered nitrogen-containing saturated heterocyclic ring, and its illustrative examples include aziridine, azetidine, pyrrolidine, piperidine, hexahydroazepine, octahydroazosine and the like, of which pyrrolidine and piperidine are preferred.

The compound (I) of the present invention may contain an asymmetric carbon atom depending on the kinds of substituents. In consequence, a mixture or isolated form of optical isomers are also included in the compound (I) of the present invention.

The compound (I) of the present invention can form acid addition salts. These salts are also included in the compound of the present invention. Their illustrative examples include acid addition salts with inorganic acids such as hydrochloric acid, hydrobromic acid, hydroiodic acid, sulfuric acid, nitric acid and phosphoric acid, organic acids such as formic acid, acetic acid, propionic acid, oxalic acid, malonic acid, succinic acid, fumaric acid, maleic acid, lactic acid, malic acid, tartaric acid, citric acid, methanesulfonic acid and ethanesulfonic acid and acidic amino acids such as aspartic acid and glutamic acid.

In addition, the compound (I) of the present invention or a pharmaceutically acceptable salt thereof may be isolated as hydrates, various types of solvates such as ethanol solvate or polymorphic forms thereof, and these various hydrates, solvates and polymorphic forms are also included in the compound of the present invention.

(Production Method)

The compound (I) of the present invention can be prepared by employing various synthetic methods making use of the characteristic properties of its basic nucleus or substituents. The typical production methods are described in the following.

Production Method 1

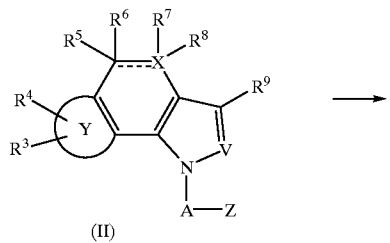

(II)

-continued

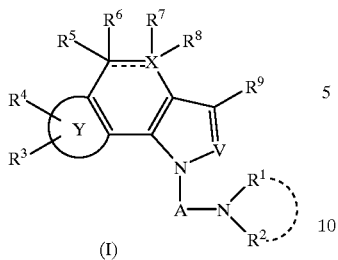

(In the above reaction scheme, $R^{1-9}$, V, X, Y, ═ and A are as defined in the foregoing, and Z means a leaving group such as a halogen atom, a tosyloxy group or a mesyloxy group.)

The compound (I) of the present invention can be produced by allowing a compound represented by the general formula (II) to react with an appropriate amine, thereby converting it into its corresponding amino compound.

This reaction can be carried out under a cooling to heating condition, if necessary in a sealed reaction tube, in the presence or absence of an appropriate solvent and if necessary in the presence of an appropriate base.

Production method 2

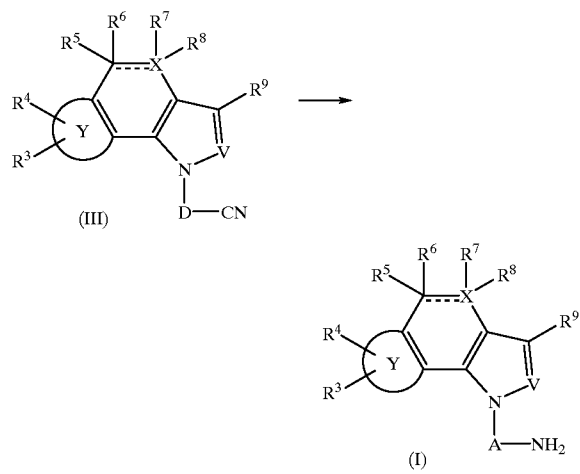

(In the above reaction scheme, $R^{3-9}$, V, X, Y, ═ and A are as defined in the foregoing, and D means an alkylene group having carbon atoms smaller by one atom than those of A.)

The compound (I) of the present invention can be produced by reducing a nitrile compound represented by the general formula (III).

This reaction can be carried out under a cooling to heating condition, preferably at room temperature, using an appropriate reducing agent in the presence or absence of an appropriate inert solvent such as diethyl ether, t-butyl methyl ether, tetrahydrofuran, dioxane, 1,2-dimethoxyethane, methylene chloride, benzene or toluene, preferably ethers (e.g., tetrahydrofuran and the like), and if necessary in the presence of an appropriate Lewis acid. Aluminum chloride or the like can be used as the Lewis acid, and complex hydride (e.g., lithium aluminum hydride) can be used as the reducing agent. Alternatively, this reaction can be carried out by catalytic hydrogenation on a metal catalyst, preferably palladium-carbon catalyst, platinum oxide or Raney nickel, using an appropriate solvent such as ethyl acetate, an alcohol, tetrahydrofuran, dioxane, acetic acid or a mixture thereof.

Production Method 3

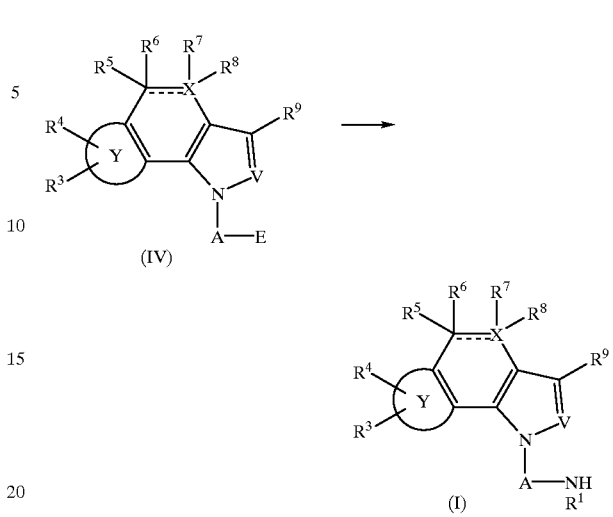

(In the above reaction scheme, $R^1$, $R^{3-9}$, V, X, Y, ═ and A are as defined in the foregoing, and E means a group which can be converted easily into an amino group, such as azido group, a nitro group or an amino group protected with a commonly used protecting group, with the proviso that A and E may together form a nitrogen-containing saturated heterocyclic ring.)

The compound (I) of the present invention can be produced by reduction or deprotection of a compound represented by the general formula (IV).

When E is an azido group or the like, this reduction can be carried out under a cooling to heating condition, preferably at room temperature, using an appropriate reducing agent in the presence or absence of the same appropriate inert solvent used in the production method 2, preferably in ether (e.g., tetrahydrofuran and the like), and if necessary in the presence of an appropriate Lewis acid such as aluminum chloride. As the reducing agent, complex hydride (e.g., lithium aluminum hydride) can be used. Alternatively, this reaction can be carried out by catalytic hydrogenation on a metal catalyst, preferably palladium-carbon catalyst, platinum oxide or Raney nickel, using an appropriate solvent such as ethyl acetate, an alcohol, tetrahydrofuran, dioxane, acetic acid or a mixture thereof, or by using triphenylphosphine.

When E is a nitro group or the like, the reduction can be carried out by catalytic hydrogenation on a metal catalyst using an appropriate solvent such as ethyl acetate, an alcohol, tetrahydrofuran, dioxane, acetic acid or a mixture thereof. Alternatively, this reaction can be carried out under a cooling to heating condition in the presence or absence of an appropriate solvent and in the presence of an acid catalyst using a metal (e.g., iron or tin).

When E is a group such as an amino group protected with a commonly used protecting group, it can be converted into amino group by carrying out its deprotection in the usual way. For example, when the protecting group is a phthalimido group, an acetamido group, or the like, a similar method described in Protecting Groups in Organic Synthesis, John Wiley & Sons, Inc. can be used, and when the protecting group is benzyloxycarbonyl group, a usual reduction method can be used.

Production Method 4

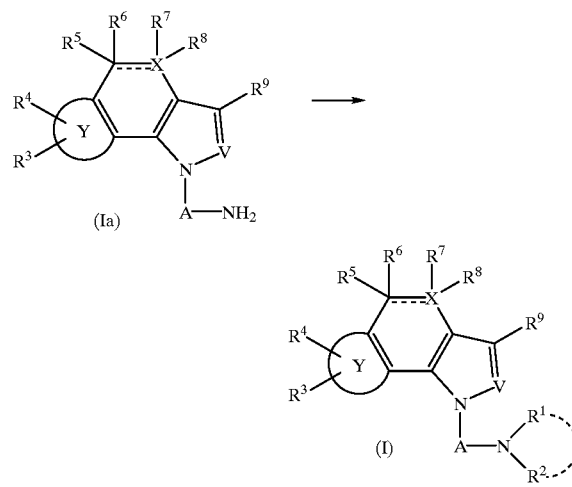

(In the above reaction scheme, $R^{1-9}$, V, X, Y, = and A are as defined in the foregoing.)

The compound (I) of the present invention can be produced by N-alkylation of the compound of general formula (Ia) produced in the production methods 2 and 3.

This reaction can be carried out under a cooling to heating condition in the presence or absence of an appropriate solvent using an appropriate alkylation agent, preferably a lower alkyl halide (e.g., propyl iodide), if necessary in the presence of an appropriate base as an acid scavenger.

Alternatively, a reductive alkylation reaction can be carried out as the alkylation reaction. That is, the starting compound can be reacted with an appropriate lower alkyl aldehyde (e.g., propanal) under a cooling to heating condition in the presence or absence of an appropriate inert solvent, using a reducing agent such as a boron hydride reagent (e.g., sodium triacetoxyborohydride), if necessary in the presence of an acid catalyst, preferably an inorganic or organic acid.

The starting material compounds of each of the aforementioned production methods 1 and 2 can be obtained easily by employing the methods of reference and Examples which will be described later, directly or modifying or applying them.

The compound of the present invention produced in this manner is isolated in its free form or as its salt. A salt of the compound of the present invention can be produced by subjecting the invention compound in the form of free base to usual salt forming reaction.

The compound (I) of the present invention or a salt thereof may also be isolated and purified as a hydrate or solvate or in its polymorphic form. Its isolation and purification can be carried out by employing generally used chemical methods such as extraction, concentration, evaporation, crystallization, filtration, recrystallization and various chromatographic techniques.

Various types of isomers can be separated by selecting appropriate starting material compound or making use of the difference in physical properties between isomers. For example, optical isomers can be prepared as stereochemically pure isomers by selecting appropriate starting material or can be separated by carrying out racemic resolution of racemic compound (e.g., a method in which a compound is derived into diastereomer salts with a general optically active acid and then subjected to optical resolution).

In addition to the compounds which will be described later in the Examples, the following compounds can be obtained without requiring special experiments, using the aforementioned production methods, the production methods of the Examples and Reference Examples of this invention, the production methods known to those skilled in the art and modifications thereof.

2-(6-Methoxy-1H-thieno[3,4-g]indazol-1-yl)ethylamine,
2-(1H-pyrazolo[3,4-e][1,2]benzisothiazol-1-yl)ethylamine,
2-(1H-pyrazolo[3,4-d]benzofurazan-1-yl)ethylamine,
2-(1H-pyrazolo[3,4-d]-2,1,3-benzothiadiazol-1-yl) ethylamine,
2-(7-methoxy-1H,6H-pyrrolo[2,3-g]indazol-1-yl) ethylamine,
2-(1H,6H-pyrazolo[3,4-e]benzimidazol-1-yl)ethylamine and
2-(1H,6H-pyrazolo[3,4-e]benzotriazol-1-yl)ethylamine.

INDUSTRIAL APPLICABILITY

Since the compound of the present invention has strong affinity and selectivity for the 5-HT$_{2C}$ receptor and is effective in animal models, it is useful for the treatment of central nervous system diseases such as sexual disorders (e.g., impotence and the like), eating disorders (e.g., obesity, bulimia, anorexia and the like), anxiety, depression and sleeping disorders.

Selectivity and affinity of the compound of the present invention for the 5-HT$_{2C}$ receptor and its evaluation in an animal model using rats were confirmed by the following methods.

A. Binding test

The 5-HT$_{2C}$ and 5-HT$_{2A}$ receptors: Carried out by [$^3$H] 5-HT binding assay in accordance with the method of A. Pazos et al., Eur. J. Pharmacol., 106, 539–546 (1985) or S. Havlik and S. J. Peroutka, Brain Res., 584, 191–196 (1992).

Using the above method, a drug concentration which inhibits 50% of receptor binding of ligand (IC$_{50}$ value) was calculated, and a Ki value which represents affinity for the receptor was obtained by the following formula.

$Ki=IC_{50}/(1+[L]/[Kd])$ ([L]: ligand concentration, [Kd]: dissociation constant)
The results are shown in Table 1.

TABLE 1

| | Binding test (Ki, nM) | |
|---|---|---|
| Test compound | 5-HT$_{2C}$ receptor | 5-HT$_{2A}$ receptor |
| Example 20 | 0.8 | 18 |
| Example 37 | 0.5 | 8.7 |
| Example 55 | 4.1 | 50 |

Thus, the compound of the present invention showed high affinity for the 5-HT$_{2C}$ receptor and about 10 times higher selectivity in comparison with that for the 5-HT$_{2A}$ receptor.

B. Animal Test Using Rats

Induction of penile erection in rats: It is known that penile erection is induced by the 5-HT$_{2C}$ receptor stimulation (Berendsen & Broekkamp, Eur. J. Pharmacol., 135, 179–184 (1987)). Test compound was administered to rats, and the frequency of penile erection during 30 minutes after the administration was measured to obtain the minimum effective dose by which statistically significant reaction was observed.

As the result, compounds showing high activity, as a minimum effective dose of from 0.003 to 1 mg/kg, sc, were found among the compounds of the present invention.

Thus, the compound of the present invention is effective in an animal model using rats and therefore is useful for the treatment of central nervous system diseases such as sexual disorders (e.g., impotence and the like).

The pharmaceutical composition which contains one or two or more of the compound (I) of the present invention, pharmaceutically acceptable salts thereof, hydrates thereof, solvates thereof and the like as the active ingredient is prepared into tablets, powders, fine granules, granules, capsules, pills, solutions, injections, suppositories, ointments, adhesive preparations and the like by using commonly used pharmaceutical carriers, fillers and other additives and administered orally (including sublingual administration) or parenterally.

Clinical dose of the compound (I) of the present invention in human is optionally decided by taking into consideration symptoms, weight, age, sex and the like of each patient to be treated, as well as the route of administration and the like, but the compound may be orally administered in a dose of generally from 10 mg to 1,000 mg, preferably from 50 mg to 200 mg, per day per adult, and the daily dose may be divided into 1 to several doses per day, or administered by intravenous injection in a dose of generally from 1 mg to 500 mg, preferably from 5 mg to 100 mg, per day per adult, and the daily dose may be divided into 1 to several doses per day or administered by intravenous drip infusion within the range of from 1 hour to 24 hours per day. Since the dosage varies under various conditions as described in the foregoing, a smaller dosage than the above range may be sufficient enough in some cases.

The solid composition for use in the oral administration according to the present invention is used in the form of tablets, powders, granules and the like. In such a solid composition, one or more active substances are mixed with at least one inert diluent such as lactose, mannitol, glucose, hydroxypropylcellulose, microcrystalline cellulose, starch, polyvinyl pyrrolidone or aluminum magnesium silicate. In the usual way, the composition may contain other additives than the inert diluent, such as lubricants (e.g., magnesium stearate), disintegrating agents (e.g., calcium cellulose glycolate), stabilizing agents (e.g., lactose) and solubilization assisting agents (e.g., glutamic acid, aspartic acid). If necessary, tablets or pills may be coated by sugar coating or with a film of a gastric or enteric substance, such as sucrose, gelatin, hydroxypropylcellulose or hydroxypropylmethylcellulose phthalate.

The liquid composition for use in oral administration includes pharmaceutically acceptable emulsions, solutions, suspensions, syrups, elixirs and the like and contains a generally used inert diluent such as purified water or ethanol. In addition to the inert diluent, this composition may also contain auxiliary agents such as a solubilizing or solubilization assisting agent, a moistening agent and a suspending agent, as well as sweeteners, flavors, aromatics and antiseptics.

The injections for use in parenteral administration include aseptic aqueous or non-aqueous solutions, suspensions and emulsions. Examples of the diluent for use in the aqueous solutions and suspensions include distilled water for injection use and physiological saline. Examples of the diluent for use in the non-aqueous solutions and suspensions include propylene glycol, polyethylene glycol, plant oil (e.g., olive oil), alcohol (e.g.,. ethanol) and polysorbate 80 (trade name). Such a composition may further contain additive agents such as a tonicity agent, an antiseptic, a moistening agent, an emulsifying agent, a dispersing agent, a stabilizing agent (e.g., lactose) and a solubilizing or solubilization assisting agent. These compositions are sterilized by filtration through a bacteria retaining filter, blending of a germicide or irradiation. Alternatively, they may be used by firstly making into sterile solid compositions and then dissolving them in sterile water or a sterile solvent for injection use prior to their use.

BEST MODE OF CARRYING OUT THE INVENTION

Examples of the present invention are given below by way of illustration and not by way of limitation. In this connection, starting material compounds to be used in the Examples are described as Reference Examples.

REFERENCE EXAMPLE 1

To a tetrahydrofuran (20 ml) solution containing 2.95 g of potassium tert-butoxy was added dropwise a tetrahydrofuran (10 ml) solution containing 2.00 g of 4-oxo-4,5,6,7-tetrahydrobenzo[b]thiophene and 3.89 g of ethyl formate under ice-cooling, and the mixture was stirred at room temperature for 30 minutes. After addition of 26 ml of 1 N hydrochloric acid to the reaction solution, 3.16 g of hydrazinoethanol was added under ice-cooling, and then the mixture was stirred at room temperature for 2 hours. The reaction solution was extracted with methylene chloride, and the organic layers were combined, washed with brine and then dried with anhydrous magnesium sulfate. After removal of the drying agent by filtration, the resulting filtrate was concentrated under a reduced pressure to give 1.56 g of 2-(4,5-dihydro-1H-thieno[2,3-g]indazol-1-yl)ethanol as a pale yellow solid.

Compounds of Reference Examples 2 to 20 were obtained in the similar manner as described in Reference Example 1.

REFERENCE EXAMPLE 2
2-(1,4-Dihydrothieno[3',2':4,5]cyclopenta[1,2-c]pyrazol-1-yl)ethanol

REFERENCE EXAMPLE 3
2-(4,5-Dihydro-1H-furo[2,3-g]indazol-1-yl)ethanol

REFERENCE EXAMPLE 4
2-(4,5-Dihydro-1H-furo[3,2-g]indazol-1-yl)ethanol

REFERENCE EXAMPLE 5
2-(4,4-Dimethyl-4,5-dihydro-1H-furo[2,3-g]indazol-1-yl)ethanol

REFERENCE EXAMPLE 6
2-(1,4-Dihydrothieno[2',3':4,5]cyclopenta[1,2-c]pyrazol-1-yl)ethanol

REFERENCE EXAMPLE 7
2-(7-Bromo-4,5-dihydro-1H-thieno[2,3-g]indazol-1-yl)ethanol

REFERENCE EXAMPLE 8
2-(7-Iodo-4,5-dihydro-1H-thieno[2,3-g]indazol-1-yl)ethanol

REFERENCE EXAMPLE 9
2-(7-Chloro-4,5-dihydro-1H-thieno[2,3-g]indazol-1-yl)ethanol

REFERENCE EXAMPLE 10
2-(7-Methoxy-4,5-dihydro-1H-thieno[2,3-g]indazol-1-yl)ethanol REFERENCE EXAMPLE 11
2-(8-Methyl-4,5-dihydro-1H-pyrazolo[3,4-e][1,2]benzisoxazol-1-yl)ethanol REFERENCE EXAMPLE 12
2-(7-Methyl-4,5-dihydro-1H-pyrazolo[3,4-e]benzothiazol-1-yl)ethanol REFERENCE EXAMPLE 13
7-Iodo-4,5-dihydro-1H-thieno[2,3-g]indazole REFERENCE EXAMPLE 14
7-Bromo-4,5-dihydro-1H-thieno[2,3-g]indazole REFERENCE EXAMPLE 15
2-(7-Methyl-4,5-dihydro-1H-thieno[2,3-g]indazol-1-yl)ethanol REFERENCE EXAMPLE 16
7-Ethyl-4,5-dihydro-1H-thieno[2,3-g]indazole REFERENCE EXAMPLE 17
2-(7-Methyl-4,5-dihydro-1H-furo[2,3-g]indazol-1-yl)ethanol REFERENCE EXAMPLE 18
7-Methyl-4,5-dihydro-1H-furo[2,3-g]indazole REFERENCE EXAMPLE 19
7-Isopropyl-4,5-dihydro-1H-thieno[2,3-g]indazole REFERENCE EXAMPLE 20
2-(7-Ethoxy-4,5-dihydro-1H-thieno[2,3-g]indazol-1-yl)ethanol

REFERENCE EXAMPLE 21

A 0.50 g of 2-(1,4-dihydrothieno[2',3':4,5]cyclopenta[1,2-c]pyrazol-1-yl)ethanol was dissolved in 15 ml of methylene chloride, 1.00 ml of triethylamine and 0.28 ml of methanesulfonyl chloride were added, and the mixture was stirred at room temperature for 1 hour. The reaction mixture was poured into ice water and extracted with chloroform. The organic layers were combined, washed with brine and then dried with anhydrous magnesium sulfate. After removal of the drying agent by filtration, the resulting filtrate was concentrated under a reduced pressure to give 0.75 g of 2-(1,4-dihydrothieno[2',3':4,5]cyclopenta[1,2-c]pyrazol-1-yl)ethyl methanesulfonate.

The compounds of Reference Examples 22 to 28 were obtained in the similar manner as described in Reference Example 21.

REFERENCE EXAMPLE 22
2-(1,4-Dihydrothieno[3',2':4,5]cyclopenta[1,2-c]pyrazol-1-yl)ethyl methanesulfonate REFERENCE EXAMPLE 23
2-(4,5-Dihydro-1H-furo[2,3-g]indazol-1-yl)ethyl methanesulfonate REFERENCE EXAMPLE 24
2-(4,4-Dimethyl-4,5-dihydro-1H-furo[2,3-g]indazol-1-yl)ethyl methanesulfonate REFERENCE EXAMPLE 25
2-(1H-Furo[2,3-g]indazol-1-yl)-1-methylethyl methanesulfonate REFERENCE EXAMPLE 26
1-(1H-Furo[2,3-g]indazol-1-ylmethyl)butyl methanesulfonate REFERENCE EXAMPLE 27
1-(1H-Furo[2,3-g]indazol-1-ylmethyl)-2-methylpropyl methanesulfonate REFERENCE EXAMPLE 28
1-Cyclohexyl-2-(1H-furo[2,3-g]indazol-1-yl)ethyl methanesulfonate

REFERENCE EXAMPLE 29

A 0.75 g of 2-(1,4-dihydrothieno[2',3':4,5]cyclopenta[1,2-c]pyrazol-1-yl)ethyl methanesulfonate was dissolved in 10 ml of dimethylformamide, 0.47 g of sodium azide was added, and the mixture was stirred at 70° C. for 17 hours. After cooling, the reaction solution was poured into ice water and extracted with ether. The organic layers were combined, washed with brine and then dried with anhydrous magnesium sulfate. After removal of the drying agent, the solvent was concentrated under a reduced pressure to give 0.56 g of 1-(2-azidoethyl)-1,4-dihydrothieno[2',3':4,5]cyclopenta[1,2-c]pyrazole.

The compounds of Reference Examples 30 to 34 were obtained in the similar manner as described in Reference Example 29.

REFERENCE EXAMPLE 30
1-(2-Azidoethyl)-1,4-dihydrothieno[3',2':4,5]cyclopenta[1,2-c]pyrazole REFERENCE EXAMPLE 31
1-(2-Azidoethyl)-4,5-dihydro-1H-furo[2,3-g]indazole REFERENCE EXAMPLE 32
1-(2-Azidoethyl)-4,4-dimethyl-4,5-dihydro-1H-furo[2,3-g]indazole REFERENCE EXAMPLE 33
1-(2-Azidopropyl)-1H-furo[2,3-g]indazole REFERENCE EXAMPLE 34
1-(2-Azido-2-cyclohexylethyl)-1H-furo[2,3-g]indazole The compounds of Reference Examples 35 to 59 were obtained in the similar manner as described in Reference Examples 21 and 29.

REFERENCE EXAMPLE 35
1-(2-Azidoethyl)-4,5-dihydro-1H-furo[3,2-g]indazole

REFERENCE EXAMPLE 36
1-(2-Azidoethyl)-7-bromo-4,5-dihydro-1H-thieno[2,3-g]indazole REFERENCE EXAMPLE 37
1-(2-Azidoethyl)-7-iodo-4,5-dihydro-1H-thieno[2,3-g]indazole REFERENCE EXAMPLE 38
1-(2-Azidoethyl)-7-chloro-4,5-dihydro-1H-thieno[2,3-g]indazole REFERENCE EXAMPLE 39
1-(2-Azidoethyl)-7-methoxy-4,5-dihydro-1H-thieno[2,3-g]indazole REFERENCE EXAMPLE 40
1-(2-Azidobutyl)-1H-furo[2,3-g]indazole REFERENCE EXAMPLE 41
1-(2-Azidoethyl)-8-methyl-4,5-dihydro-1H-pyrazolo[3,4-e][1,2]benzisoxazole

REFERENCE EXAMPLE 42
1-(2-Azidoethyl)-7-methyl-4,5-dihydro-1H-pyrazolo[3,4-e]benzothiazole

REFERENCE EXAMPLE 43
1-(2-Azidoethyl)-4,5-dihydro-1H-thieno[2,3-g]indazole

REFERENCE EXAMPLE 44
(S)-1-(2-Azidopropyl)-1H-pyrazolo[3,4-e]benzoxazole

REFERENCE EXAMPLE 45
(S)-1-(2-Azidopropyl)-7-methyl-1H-pyrazolo[3,4-e]benzoxazole

REFERENCE EXAMPLE 46
(S)-1-(2-Azidopropyl)-1H-thieno[2,3-g]indazole

REFERENCE EXAMPLE 47
(S)-1-(2-Azidopropyl)-7-bromo-1H-thieno[2,3-g]indazole

REFERENCE EXAMPLE 48
(S)-1-(2-Azidopropyl)-7-iodo-1H-thieno[2,3-g]iindazole

REFERENCE EXAMPLE 49
(S)-1-(2-Azidopropyl)-7-chloro-1H-thieno[2,3-g]indazole

REFERENCE EXAMPLE 50
1-(2-Azidoethyl)-7-methyl-4,5-dihydro-1H-thieno[2,3-g]indazole

REFERENCE EXAMPLE 51
(S)-1-(2-Azidopropyl)-7-methyl-1H-thieno[2,3-g]indazole

REFERENCE EXAMPLE 52
(S)-1-(2-Azidopropyl)-7-ethyl-1H-thieno[2,3-g]indazole

REFERENCE EXAMPLE 53
(S)-1-(2-Azidopropyl)-7-methyl-1H-furo[2,3-g]indazole

REFERENCE EXAMPLE 54
(S)-1-(2-Azidopropyl)-7-isopropyl-1H-thieno[2,3-g]indazole

REFERENCE EXAMPLE 55
1-(2-Azidoethyl)-7-ethoxy-4,5-dihydro-1H-thieno[2,3-g]indazole

REFERENCE EXAMPLE 56
(S)-1-(2-Azidopropyl)-3-ethyl-1H-furo[2,3-g]indazole

REFERENCE EXAMPLE 57
(S)-1-(2-Azidopropyl)-3-propyl-1H-furo[2,3-g]indazole

REFERENCE EXAMPLE 58
(S)-1-(2-Azidopropyl)-3-methoxy-1H-furo[2,3-g]indazole

REFERENCE EXAMPLE 59
1-(2-Azidocyclohexyl)-1H-furo[2,3-g]indazole

REFERENCE EXAMPLE 60

A 1.00 g of 1-(2-azidoethyl)-4,5-dihydro-1H-thieno[2,3-g]indazole was dissolved in 30 ml of dioxane, 2.80 g of 2,3-dichloro-5,6-dicyano-1,4-benzoquinone was added at room temperature, and the mixture was heated under reflux for 8 hours. The reaction mixture was cooled, poured into sodium bicarbonate aqueous solution and then extracted with chloroform. The organic layers were combined and dried with anhydrous magnesium sulfate. After removal of the drying agent by filtration, the solvent was concentrated under a reduced pressure, and the resulting residue was purified by a silica gel column chromatography to give 0.73 g of 1-(2-azidoethyl)-1H-thieno[2,3-g]indazole as a pale brown oil.

The compounds of Reference Examples 61 to 74 were obtained in the similar manner as described in Reference Example 60.

REFERENCE EXAMPLE 61
1-(2-Azidoethyl)-7-bromo-1H-thieno[2,3-g]indazole

REFERENCE EXAMPLE 62
1-(2-Azidoethyl)-7-iodo-1H-thieno[2,3-g]indazole

REFERENCE EXAMPLE 63
1-(2-Azidoethyl)-8-methyl-1H-pyrazolo[3,4-e][1,2]benzisoxazole

REFERENCE EXAMPLE 64
1-(2-Azidoethyl)-7-methyl-1H-pyrazolo[3,4-e]benzothiazole

REFERENCE EXAMPLE 65
7-Iodo-1H-thieno[2,3-g]indazole

REFERENCE EXAMPLE 66
7-Bromo-1H-thieno[2,3-g]indazole

REFERENCE EXAMPLE 67
7-Chloro-1H-thieno[2,3-g]indazole

REFERENCE EXAMPLE 68
1-(2-Azidoethyl)-7-methyl-1H-thieno[2,3-g]indazole

REFERENCE EXAMPLE 69
7-Methyl-1H-thieno[2,3-g]indazole

REFERENCE EXAMPLE 70
7-Ethyl-1H-thieno[2,3-g]indazole

REFERENCE EXAMPLE 71
7-Methyl-1H-furo[2,3-g]indazole

REFERENCE EXAMPLE 72
7-Isopropyl-1H-thieno[2,3-g]indazole

REFERENCE EXAMPLE 73
1-(2-Azidoethyl)-7-ethoxy-1H-thieno[2,3-g]indazole

REFERENCE EXAMPLE 74
N-[2-(1H-Thieno[2,3-g]indazol-1-yl)ethyl]acetamide

Compounds of Reference examples 75 and 76 were obtained in the similar manner as described in Reference Examples 1 and 60.

REFERENCE EXAMPLE 75
7-Methoxy-1H-thieno[2,3-g]indazole

REFERENCE EXAMPLE 76
7-tert-Butyl-1H-thieno[2,3-g]indazole

Compounds of Reference examples 77 and 78 were obtained by the usual acetylation reaction.

REFERENCE EXAMPLE 77
N-[2-(4,5-Dihydro-1H-furo[2,3-g]indazol-1-yl)ethyl]acetamide

REFERENCE EXAMPLE 78
N-[2-(4,5-Dihydro-1H-furo[3,2-g]indazol-1-yl)ethyl]acetamide

REFERENCE EXAMPLE 79

A 15 ml of dimethylformamide was added to 0.72 g of sodium hydride under argon atmosphere, 2.60 g of 1H-furo[2,3-g]indazole which had been obtained in the similar manner as described in Reference Examples 1 and 60 was added dropwise, and the resulting mixture was stirred for 30 minutes. After cooling the reaction mixture with ice-bath, a 2.10 ml of ethyl bromoacetate was added, and the resulting mixture was stirred at room temperature for 2 hours. The reaction solution was poured into ice water and extracted with ethyl acetate. The organic layers were combined, washed with brine and then dried with anhydrous magnesium sulfate. After removal of the solvent, the residue was purified by a silica gel column chromatography to give 2.70 g of (1H-furo[2,3-g]indazol-1-yl)ethyl acetate.

REFERENCE EXAMPLE 80

A 0.44 g of lithium aluminum hydride was suspended in 50 ml of tetrahydrofuran under argon atmosphere, a tetrahydrofuran (10 ml) solution containing 2.60 g of (1H-furo[2,3-g]indazol-1-yl)ethyl acetate was added dropwise, and the resulting mixture was stirred at room temperature for 1 hour. The reaction solution was cooled in an ice bath, methanol was added to decompose excess lithium aluminum hydride, and then 0.44 ml of water, 0.44 ml of 15% sodium hydroxide aqueous solution and 1.30 ml of water were added in that order. The resulting mixture was stirred for 30 minutes, anhydrous magnesium sulfate and celite were added, followed by stirring for 30 minutes. After removal of the insoluble matter by celite filtration, the filtrate was concentrated under a reduced pressure to give 1.82 g of 2-(1H-furo[2,3-g]indazol-1-yl)ethanol.

REFERENCE EXAMPLE 81

A dimethyl sulfoxide (15 ml) solution containing 4.20 ml of triethylamine and 4.74 g of $SO_3$-pyridine complex was added to a dimethyl sulfoxide (15 ml) solution containing 1.80 g of 2-(1H-furo[2,3-g]indazol-1-yl)ethanol, and the resulting mixture was stirred at room temperature for 30 minutes. The reaction solution was poured into water, acidified with 1 N hydrochloric acid and then extracted with ethyl acetate. The organic layers were combined, washed with brine and then dried with anhydrous magnesium sulfate. After removal of the drying agent by filtration, the solvent was concentrated under a reduced pressure, and the residue was purified by a silica gel column chromatography to give 0.89 g of (1H-furo[2,3-g]indazol-1-yl)acetaldehyde.

REFERENCE EXAMPLE 82

Under argon atmosphere, a dimethylformamide (5 ml) solution containing 1.00 g of 1H-furo(2,3-g]indazole was added dropwise to a dimethylformamide (10 ml) solution containing 0.27 g of sodium hydride under cooling with ice-bath, and the mixture was stirred for 30 minutes. A 0.52 ml of propylene oxide was added to the reaction mixture under ice-cooling, and the mixture was stirred at room temperature for 41 hours. The reaction mixture was poured into ice water and extracted with ethyl acetate. The organic layers were combined, washed with brine and then dried with anhydrous magnesium sulfate. After removal of the solvent, the residue was purified by a silica gel column chromatography to give 0.59 g of 1-(1H-furo[2,3-g]indazol-1-yl)propan-2-ol.

Compounds of Reference Examples 83 to 97 were obtained in the similar manner as described in reference Example 82.

REFERENCE EXAMPLE 83
(R)-1-(1H-Pyrazolo[3,4-e]benzoxazol-1-yl)-2-propanol

REFERENCE EXAMPLE 84
(R)-1-(7-Methyl-1H-pyrazolo[3,4-e]benzoxazol-1-yl)-2-propanol

REFERENCE EXAMPLE 85
(R)-1-(1H-Thieno[2,3-g]indazol-1-yl)-2-propanol

REFERENCE EXAMPLE 86
(R)-1-(7-Bromo-1H-thieno[2,3-g]indazol-1-yl)-2-propanol

REFERENCE EXAMPLE 87
(R)-1-(7-Iodo-1H-thieno[2,3-g]indazol-1-yl)-2-propanol

REFERENCE EXAMPLE 88
(R)-1-(7-Chloro-1H-thieno[2,3-g]indazol-1-yl)-2-propanol

REFERENCE EXAMPLE 89
(R)-1-(7-Methyl-1H-thieno[2,3-g]indazol-1-yl)-2-propanol

REFERENCE EXAMPLE 90
(R)-1-(7-Ethyl-1H-thieno[2,3-g]indazol-1-yl)-2-propanol

REFERENCE EXAMPLE 91
(R)-1-(7-Methyl-1H-furo[2,3-g]indazol-1-yl)-2-propanol

REFERENCE EXAMPLE 92
(R)-1-(7-Isopropyl-1H-thieno[2,3-g]indazol-1-yl)-2-propanol

REFERENCE EXAMPLE 93
(R)-1-(3-Methoxy-1H-furo[2,3-g]indazol-1-yl)-2-propanol

REFERENCE EXAMPLE 94
(S)-1-(1H-Furo[2,3-g]indazol-1-yl)-2-propanol

REFERENCE EXAMPLE 95
1-(1H-Furo[2,3-g]indazol-1-yl)-3,3,3-trifluoro-2-propanol

REFERENCE EXAMPLE 96
1-(1H-Furo[2,3-g]indazol-1-yl)-2-cyclohexanol

REFERENCE EXAMPLE 97
(R)-1-(3-Ethyl-1H-furo[2,3-g]indazol-1-yl)-2-propanol

REFERENCE EXAMPLE 98

(S)-1-(2-Azidopropyl)-1H-furo[2,3-g]indazole was obtained in the similar manner as described in Reference Examples 82, 21 and 29.

REFERENCE EXAMPLE 99

Under argon atmosphere, 5 ml of 1.0 M tetrahydrofuran solution of ethylmagnesium bromide was diluted with 5 ml of tetrahydrofuran, a tetrahydrofuran (5 ml) solution of 0.30 g of (1H-furo[2,3-g]indazol-1-yl)acetaldehyde was added dropwise, and the mixture was stirred at room temperature for 3 days. The reaction mixture was poured into ammonium chloride aqueous solution and extracted with ethyl acetate. The organic layers were combined, washed with brine and then dried with anhydrous magnesium sulfate. After removal of the solvent, the residue was purified by a silica gel column chromatography to give 0.29 g of 1-(1H-furo[2,3-g]indazol-1-yl)-2-butanol.

Compounds of Reference examples 100 to 102 were obtained in the similar manner as described in Reference Example 99.

REFERENCE EXAMPLE 100
1-(1H-Furo[2,3-g]indazol-1-yl)-2-pentanol

REFERENCE EXAMPLE 101
1-(1H-Furo[2,3-g]indazol-1-yl)-3-methyl-2-butanol

REFERENCE EXAMPLE 102
1-Cyclohexyl-2-(1H-furo[2,3-g)indazol-1-yl)ethanol

REFERENCE EXAMPLE 103

A 4.20 g of sodium periodate was added gradually to a mixture of 1.80 g of 5-allyl-4-oxo-4,5,6,7-tetrahydrobenzo[b]thiophene, 25 mg of osmium tetraoxide, 15 ml of water and 45 ml of dioxane, while keeping the reaction mixture at 24 to 26° C., and then the mixture was stirred at room temperature for 3 hours. After extraction of the reaction mixture with ethyl acetate, the organic layers were combined, washed with 2% sodium thiosulfate aqueous solution, water and brine in that order and then dried with anhydrous magnesium sulfate. After removal of the drying agent, the solvent was concentrated under a reduced pressure, and the resulting residue was purified by a silica gel column chromatography to give 1.33 g of (4-oxo-4,5,6,7-tetrahydrobenzo[b]thiophen-5-yl)acetaldehyde. A 1.32 g of the aldehyde compound and 1.39 g of N-acetylethylenediamine were dissolved in 50 ml of toluene. Then, 10 mg of camphorsulfonic acid was added, and the mixture was heated under reflux for 3 hours while removing the produced water. After cooling, the reaction solution was poured into ice-cooled saturated sodium bicarbonate aqueous solution and extracted with ethyl acetate. The organic layers were combined, the drying agent was removed by filtration and then the solvent was concentrated under a reduced pressure to give 1.38 g of N-(2-(4,5-dihydro-1H-thieno[2,3-g]indol-1-yl)ethyl]acetaamide. From this compound, N-[2-(1H-thieno[2,3-g]indol-1-yl)ethyl]acetamide was obtained in the similar manner as described in Reference Example 60.

Compounds of Reference examples 104 to 115 were obtained in the similar manner as described in Reference Example 79.

REFERENCE EXAMPLE 104
2-(1H-Furo[2,3-g]indazol-1-yl)propionitrile

REFERENCE EXAMPLE 105
2-(1H-Furo[2,3-g]indazol-1-yl)acetophenone

REFERENCE EXAMPLE 106
2-(1H-Furo[2,3-g]indazol-1-yl)cyclopentanone

REFERENCE EXAMPLE 107
2-(3-Ethyl-1H-furo[2,3-g]indazol-1-yl)acetonitrile

REFERENCE EXAMPLE 108
2-(1,5,6,7-Tetrahydrocyclopenta[f]indazol-1-yl)acetonitrile

REFERENCE EXAMPLE 109
(7-Ethyl-1H-furo[2,3-g]indazol-1-yl)acetonitrile

REFERENCE EXAMPLE 110
(7-Isopropyl-1H-thieno[2,3-g]indazol-1-yl)acetonitrile

REFERENCE EXAMPLE 111
(1-(2-Methyl-2-nitro-1-propyl)-1H-furo[2,3-g]indazole

REFERENCE EXAMPLE 112
1-(1-t-Butoxycarbonylazetidin-3-ylmethyl)-1H-furo[2,3-g]indazole

REFERENCE EXAMPLE 113
1-(1-t-Butoxycarbonylazetidin-2-ylmethyl)-1H-furo[2,3g]indazole

REFERENCE EXAMPLE 114
1-(1-Benzylpiperidin-3-ylmethyl)-1H-furo[2,3-g]indazole

REFERENCE EXAMPLE 115
2-(1H-Pyrazolo[4,3-h]quinolin-1-yl)acetonitrile

REFERENCE EXAMPLE 116

A 0.40 g of 6-hydroxy-7-aminoindazole was mixed with 10 ml of ethyl orthoformate and heated under reflux for 2 hours. After cooling of the reaction solution, the solvent was evaporated under a reduced pressure and the residue was purified by a silica gel column chromatography to give 0.31 g of 1H-pyrazolo[3,4-e]benzoxazole.

REFERENCE EXAMPLE 117

7-Methyl-1H-pyrazolo[3,4-e]benzoxazole was obtained in the similar manner as described in Reference Example 116.

REFERENCE EXAMPLE 118

Triethylsilane (0.56 ml) was added to a trifluoroacetic acid (2 ml) solution containing 0.20 g of cyclopenta[f]indazol-7-1H-one under ice-cooling, and the mixture was stirred at room temperature for 14 hours. The solvent was evaporated under a reduced pressure, the resulting residue was extracted using chloroform and washed with 1 N sodium hydroxide aqueous solution, and the thus obtained organic layer was dried with anhydrous sodium sulfate. After removal of the drying agent, the solvent was evaporated and the residue was purified by a silica gel column chromatography to give 0.08 g of 1,5,6,7-tetrahydrocyclopenta[f]indazole.

REFERENCE EXAMPLE 119

Hydrazine monohydrate was added to an ethanol (50 ml) solution of 3.00 g 5-ethoxycarbonyl-4-oxo-4,5,6,7-tetrahydrobenzo[b]furan, and the mixture was stirred at room temperature for 14 hours. The solvent was evaporated under a reduced pressure, and the residue was washed with hexane/ethyl acetate and dried under a reduced pressure to give 4,5-dihydro-3-hydroxy-1H-furo[2,3-g]indazole. Diazomethane (2 eq.) was added to a mixed solution of 1,4-dioxane (10 ml) and methanol (20 ml) containing 1.50 g of the thus obtained compound, and the mixture was stirred at room temperature for 1 hour. Acetic acid was added to the reaction mixture until gas evolution stopped, and then the solvent was evaporated under a reduced pressure. The residue was extracted with chloroform and washed with saturated sodium bicarbonate aqueous solution, and the thus obtained organic layer was dried over anhydrous sodium sulfate. After removal of the drying agent, the solvent was evaporated and the residue was purified by a silica gel column chromatography to give 0.80 g of 4,5-dihydro-3-methoxy-1H-furo[2,3-g]indazole. From this compound, 3-methoxy-1H-furo[2,3-g]indazole was obtained in the similar manner as described in Reference Example 60.

Compounds of Reference examples 120 and 121 were obtained in the similar manner as described in Reference Example 1.

REFERENCE EXAMPLE 120
7-Chloro-4,5-dihydro-1H-thieno[2,3-g]indazole

REFERENCE EXAMPLE 121
7-Methyl-4,5-dihydro-1H-thieno[2,3-g]indazole

Compounds of Reference examples 122 to 124 were obtained in the similar manner as described in Reference Examples 1 and 60.

REFERENCE EXAMPLE 122
3-Methyl-1H-furo[2,3-g]indazole

REFERENCE EXAMPLE 123
3-Propyl-1H-furo[2,3-g]indazole

REFERENCE EXAMPLE 124
3-Ethyl-1H-furo[2,3-g]indazole

REFERENCE EXAMPLE 125
1-(2-Azido-3,3,3-trifluoropropyl)-1H-furo[2,3-g]indazole was obtained in the similar manner as described in Reference Examples 21 and 29.

EXAMPLE 1

Under argon atmosphere, 0.18 g of lithium aluminum hydride was suspended in 10 ml of tetrahydrofuran, a tetrahydrofuran (5 ml) solution of 0.56 g 1-(2-azidoethyl)-1,4-dihydrothieno[2',3':4,5]cyclopenta[1,2-c]pyrazole was added under ice-cooling, followed by stirring for 30 minutes. Methanol was added to decompose excess lithium aluminum hydride, and 0.18 ml of water, 0.18 ml of 15% sodium hydroxide aqueous solution and 0.54 ml of water were added in that order. The resulting mixture was stirred for 30 minutes, anhydrous magnesium sulfate and celite were added, and the mixture was stirred for 30 minutes. After removal of the thus formed insoluble matter by celite filtration and subsequent concentration of the resulting filtrate, the thus obtained residue was purified by a silica gel column chromatography (eluent: chloroform/methanol=95/5) and dissolved in a mixed solvent of ethanol and ethyl acetate. Ethyl acetate solution of 4 N hydrochloric acid was added to the resulting solution, and then the resulting crystals were collected by filtration and dried under a reduced pressure to give 0.42 g of 2-(1,4-dihydrothieno[2',3':4,5]cyclopenta[1,2-c]pyrazol-1-yl)ethylamine hydrochloride.

Compounds of Examples 2 to 13 were obtained in the similar manner as described in Example 1.

EXAMPLE 2
2-(1,4-Dihydrothieno[3',2':4,5]cyclopenta[1,2-c]pyrazol-1-yl)ethylamine hydrochloride Starting material: 1-(2-Azidoethyl)-1,4-dihydrothieno[3',2':4,5]cyclopenta[1,2-pyrazole

EXAMPLE 3
2-(4,5-Dihydro-1H-furo[2,3-g]indazol-1-yl)ethylamine hydrochloride Starting material: 1-(2-Azidoethyl)-4,5-dihydro-1H-furo[2,3-g]indazole

EXAMPLE 4
2-(4,5-Dihydro-1H-furo[3,2-g]indazol-1-yl)ethylamine hydrochloride Starting material: 1-(2-Azidoethyl)-4,5-dihydro-1H-furo[3,2-g]indazole

EXAMPLE 5
2-(4,4-Dimethyl-4,5-dihydro-1H-furo[2,3-g]indazol-1-yl)ethylamine hydrochloride Starting material: 1-(2-Azidopropyl)-4,4-dimethyl-4,5-dihydro-1H-furo[2,3-g]indazole

EXAMPLE 6
2-(4,5-Dihydro-1H-thieno[2,3-g]indazol-1-yl)ethylamine hydrochloride Starting material: 1-(2-Azidoethyl)-4,5-dihydro-1H-thieno[2,3-g]indazole

EXAMPLE 7
2-(1H-Furo[2,3-g]indazol-1-yl)-1-methylethylamine hydrochloride

Starting material: 1-(2-Azidopropyl)-1H-furo[2,3-g]indazole

EXAMPLE 8
1-Ethyl-2-(1H-furo[2,3-g]indazol-1-yl)ethylamine hydrochloride

Starting material: 1-(2-Azidobutyl)-1H-furo[2,3-g]indazole

EXAMPLE 9
1-Cyclohexyl-2-(1H-furo[2,3-g]indazol-1-yl)ethylamine hydrochloride

EXAMPLE 10
2-(1H-Thieno[2,3-g]indazol-1-yl)ethylamine hydrochloride
Starting material: 1-(2-Azidoethyl)-1H-thieno[2,3-g]indazole

EXAMPLE 11
(S)-2-(1H-Furo[2,3-g]indazol-1-yl)-1-methylethylamine hydrochloride Starting material: (S)-1-(2-Azidopropyl)-1H-furo[2,3-g]indazole

EXAMPLE 12
2-(1H-Furo[2,3-g]indazol-1-yl)-1-trifluoromethylethylamine hydrochloride

EXAMPLE 13
2-(1H-Furo[2,3-g]indazol-1-yl)cyclohexylamine fumarate
Compounds of Examples 14 and 15 were obtained in the similar manner as described in Reference Examples 82, 21 and 29 and Example 1.

EXAMPLE 14
(S)-2-(7-Methoxy-1H-thieno[2,3-g]indazol-1-yl)-1-methylethylamine fumarate Starting material: 7-Methoxy-1H-thieno[2,3-g]indazole and (R)-propylene oxide

EXAMPLE 15
(S)-2-(7-tert-Butyl-1H-thieno[2,3-g]indazol-1-yl)-1-methylethylamine hydrochloride Starting material: 7-tert-Butyl-1H-thieno[2,3-g]indazole and (R)-propylene oxide

EXAMPLE 16
2-(8-tert-Butyl-1H-thieno[2,3-g]indazol-1-yl)ethylamine hydrochloride was obtained from 3-tert-butyl-4-oxo-4,5,6,7-tetrahydrobenzo[b]thiophene in the similar manner as described in Reference Examples 1, 21, 29 and 60 and Example 1.

EXAMPLE 17
2-(7-Methyl-1H-furo[2,3-g]indazol-1-yl)ethylamine hydrochloride was obtained from 2-(7-methyl-4,5-dihydro- 1H-furo[2,3-g]indazol-1-yl)ethanol in the similar manner as described in Reference Examples 21, 29 and 60 and Example 1.

EXAMPLE 18

(R)-2-(1H-Furo[2,3-g]indazol-1-yl)-1-methylethylamine dihydrochloride was obtained from (S)-1-(1H-furo[2,3-g]indazole-1-yl)-2-propanol in the similar manner as described in Reference Examples 21 and 29 and Example 1.

EXAMPLE 19

A 0.32 g of I-(2-azidoethyl)-7-bromo-4,5-dihydro-1H-thieno[2,3-g]indazole was dissolved in 10 ml of tetrahydrofuran, 0.31 g of triphenylphosphine was added, followed by stirring at room temperature for 1 hour. Then, 0.31 g of triphenylphosphine was added and the mixture was heated under reflux for 1 hour. Then, 0.03 g of water was added and the mixture was heated under reflux for 8 hours. After cooling, the reaction mixture was acidified by addition of 1 N hydrochloric acid and then extracted with chloroform. The thus obtained water layer was alkalified with 40% sodium hydroxide aqueous solution and extracted with chloroform. The organic layers were combined and dried with anhydrous magnesium sulfate. After removal of the drying agent by filtration, the solvent was concentrated under a reduced pressure, the resulting residue was purified by a silica gel column chromatography (eluent: chloroform/methanol/saturated aqueous ammonia=20/1/0.1–10/1/0.1) and dissolved in 1.5 ml of ethanol, 0.15 ml of 4 N hydrochloric acid ethyl acetate solution was added, and the resulting crystals were collected by filtration and dried under a reduced pressure to give 0.16 g of 2-(7-bromo-4,5-dihydro-1H-thieno[2,3-g]indazol-1-yl)ethylamine hydrochloride.

Compounds of Examples 20 to 42 were obtained in the similar manner as described in Example 19.

EXAMPLE 20

2-(7-Bromo-1H-thieno[2,3-g]indazol-1-yl)ethylamine hydrochloride

Starting material: 1-(2-Azidoethyl)-7-bromo-1H-thieno[2,3-g]indazole

EXAMPLE 21

2-(8-Methyl-4,5-dihydro-1H-pyrazolo[3,4-e][1,2]benzisoxazol-1-yl)ethylamine hydrochloride

EXAMPLE 22

2-(7-Methyl-1H-pyrazolo[3,4-e]benzothiazol-1-yl)ethylamine hydrochloride

EXAMPLE 23

(S)-1-Methyl-2-(1H-pyrazolo[3,4-e]benzoxazol-1-yl)ethylamine fumarate

EXAMPLE 24

(S)-1-Methyl-2-(7-methyl-1H-pyrazolo[3,4-e]benzoxazol-1-yl)ethylamine fumarate

EXAMPLE 25

(S)-1-Methyl-2-(1H-thieno[2,3-g]indazol-1-yl)ethylamine fumarate

Starting material: (S)-1-(2-Azidopropyl)-1H-thieno[2,3-g]indazole

EXAMPLE 26

(S)-2-(7-Bromo-1H-thieno[2,3-g]indazol-1-yl)-1-methylethylamine fumarate

Starting material: (S)-1-(2-Azidopropyl)-7-bromo-1H-thieno[2,3-g]indazole

EXAMPLE 27

(S)-2-(7-Iodo-1H-thieno[2,3-g]indazol-1-yl)-1-methylethylamine fumarate

Starting material: (S)-1-(2-Azidopropyl)-7-iodo-1H-thieno[2,3-g]indazole

EXAMPLE 28

(S)-2-(7-Chloro-1H-thieno[2,3-g]indazol-1-yl)-1-methylethylamine fumarate

Starting material: (S)-1-(2-Azidopropyl)-7-chloro-1H-thieno[2,3-g]indazole

EXAMPLE 29

2-(7-Methyl-1H-thieno[2,3-g]indazol-1-yl)ethylamine fumarate

Starting material: 1-(2-Azidoethyl)-7-methyl-1H-thieno[2,3-g]indazole

EXAMPLE 30

(S)-1-Methyl-2-(7-methyl-1H-thieno[2,3-g]indazol-1-yl)ethylamine fumarate

Starting material: (S)-1-(2-Azidopropyl)-7-methyl-1H-thieno[2,3-g]indazole

EXAMPLE 31

(S)-2-(7-Ethyl-1H-thieno[2,3-g]indazol-1-yl)-1-methylethylamine fumarate

Starting material: (S)-1-(2-Azidopropyl)-7-ethyl-1H-thieno[2,3-g]indazole

EXAMPLE 32

(S)-1-Methyl-2-(7-methyl-1H-furo[2,3-g]indazol-1-yl)ethylamine fumarate

Starting material: (S)-1-(2-Azidopropyl)-7-methyl-1H-furo[2,3-g]indazole

EXAMPLE 33

(S)-2-(7-Isopropyl-1H-thieno[2,3-g]indazol-1-yl)-1-methylethylamine fumarate

Starting material: (S)-1-(2-Azidopropyl)-7-isopropyl-1H-thieno[2,3-g]indazole

EXAMPLE 34

2-(7-Ethoxy-1H-thieno[2,3-g]indazol-1-yl)ethylamine hydrochloride

Starting material: 1-(2-Azidoethyl)-7-ethoxy-1H-thieno[2,3-g]indazole

EXAMPLE 35

(S)-2-(3-Ethyl-1H-furo[2,3-g]indazol-1-yl)-1-methylethylamine dihydrochloride

Starting material: (S)-1-(2-Azidopropyl)-3-ethyl-1H-furo[2,3-g]indazole

EXAMPLE 36

(S)-1-Methyl-2-(3-propyl-1H-furo[2,3-g]indazol-1-yl)ethylamine dihydrochloride

Starting material: (S)-1-(2-Azidopropyl)-3-propyl-1H-furo[2,3-g]indazole

EXAMPLE 37

(S)-2-(3-Methoxy-1H-furo[2,3-g]indazol-1-yl)-1-methylethylamine fumarate

Starting material: (S)-1-(2-Azidopropyl)-3-methoxy-1H-furo[2,3-g]indazole

EXAMPLE 38

2-(7-Iodo-4,5-dihydro-1H-thieno[2,3-g]indazol-1-yl)ethylamine hydrochloride

Starting material: 1-(2-Azidoethyl)-7-iodo-4,5-dihydro-1H-thieno[2,3-g]indazole

EXAMPLE 39

2-(7-Iodo-1H-thieno[2,3-g]indazol-1-yl)ethylamine hydrochloride

Starting material: 1-(2-Azidoethyl)-7-iodo-1H-thieno[2,3-g]indazole

EXAMPLE 40

2-(8-Methyl-1H-pyrazolo[3,4-e][1,2]benzisoxazol-1-yl)ethylamine hydrochloride

Starting material: 1-(2-Azidoethyl)-8-methyl-1H-pyrazolo[3,4-e][1,2]benzisoxazole

EXAMPLE 41

2-(7-Methoxy-4,5-dihydro-1H-thieno[2,3-g]indazol-1-yl)ethylamine hydrochloride

Starting material: 1-(2-Azidoethyl)-7-methoxy-4,5-dihydro-1H-thieno[2,3-g]indazole

EXAMPLE 42

2-(7-Chloro-4,5-dihydro-1H-thieno[2,3-g]indazol-1-yl)ethylamine hydrochloride

Starting material: 1-(2-Azidoethyl)-7-chloro-4,5-dihydro-1H-thieno[2,3-g]indazole

EXAMPLE 43

A 1.60 g of potassium hydroxide was added to an ethylene glycol (20 ml) solution containing 0.51 g of [2-(1H-furo[2,3-g]indazol-1-yl)ethyl]acetamide, and the mixture was stirred at 170° C. for 2 hours. The reaction solution was cooled, diluted with water and then extracted with ethyl acetate. The organic layers were combined, washed with water and brine and then dried over anhydrous magnesium sulfate. After removal of the drying agent by filtration, the filtrate was concentrated and the thus obtained residue was purified by a silica gel column chromatography (eluent: chloroform/methanol =95/5) to give 2-(1H-furo[2,3-g]indazol-1-yl)ethylamine. The thus obtained 2-(1H-furo[2,3-g]indazol-1-yl)ethylamine was dissolved in a mixture of ethanol and ethyl acetate, 4 N hydrochloric acid ethyl acetate solution was added to the resulting solution, and the resulting crystals were collected by filtration and dried under a reduced pressure to give 0.06 g of 2-(1H-furo[2,3-g]indazol-1-yl)ethylamine hydrochloride.

EXAMPLE 44

2-(1H-Furo[3,2-g]indazol-1-yl)ethylamine hydrochloride was obtained from N-[2-(4,5-dihydro-1H-furo(3,2-g]indazol-1-yl)ethyl]acetamide in the similar manner as described in Reference Example 60 and Example 43.

Compounds of Examples 45 and 46 were obtained in the similar manner as described in Reference Example 29 and Example 1.

EXAMPLE 45

1-(1H-Furo[2,3-g]indazol-1-ylmethyl)butylamine hydrochloride

EXAMPLE 46

1-(1H-Furo[2,3-g]indazol-1-ylmethyl)-2-methylpropylamine hydrochloride

Compounds of Examples 47 and 48 were obtained in the similar manner as described in Reference Example 60 and Example 19.

EXAMPLE 47

2-(7-Methoxy-1H-thieno[2,3-g]indazol-1-yl)ethylamine hydrochloride

Starting material: 1-(2-Azidoethyl)-7-methoxy-4,5-dihydro-1H-thieno[2,3-g]indazole

EXAMPLE 48

2-(7-Chloro-1H-thieno[2,3-g]indazol-1-yl)ethylamine hydrochloride

Starting material: 1-(2-Azidoethyl)-7-chloro-4,5-dihydro-1H-thieno[2,3-g]indazole

EXAMPLE 49

2-(1H-Thieno[2,3-g]indol-1-yl)ethylamine was obtained in the similar manner as described in Example 43.

Compounds of Examples 50 to 55 were obtained in the similar manner as described in Example 1.

EXAMPLE 50

2-(1H-Furo[2,3-g]indazol-1-yl)propylamine hydrochloride

Starting material: 2-(1H-Furo[2,3-g]indazol-1-yl)propionitrile

EXAMPLE 51

2-(1H-Pyrazolo[4,3-h]quinolin-1-yl)ethylamine fumarate

Starting material: 2-(1H-Pyrazolo[4,3-h]quinolin-1-yl)acetonitrile

EXAMPLE 52

2-(1,5,6,7-Tetrahydrocyclopenta[f]indazol-1-yl)ethylamine dihydrochloride

EXAMPLE 53

2-(7-Ethyl-1H-thieno[2,3-g]indazol-1-yl)ethylamine fumarate

Starting material: (7-Ethyl-1H-thieno[2,3-g]indazol-1-yl)acetonitrile

EXAMPLE 54

2-(7-Isopropyl-1H-thieno[2,3-g]indazol-1-yl)ethylamine fumarate

Starting material: (7-Isopropyl-1H-thieno[2,3-g]indazol-1-yl)acetonitrile

EXAMPLE 55

2-(3-Ethyl-1H-furo[2,3-g]indazol-1-yl)ethylamine dihydrochloride

Starting material: 2-(3-Ethyl-1H-furo[2,3-g]indazol-1-yl)acetonitrile

Compounds of Examples 56 and 57 were obtained in the similar manner as described in Reference Example 79 and Example 1.

EXAMPLE 56

2-(7,8-Dihydro-1H-furo[2,3-g]indazol-1-yl)ethylamine fumarate

Starting material: 7,8-Dihydro-1H-furo[2,3-g]indazole

EXAMPLE 57

2-(7-tert-Butyl-1H-thieno[2,3-g]indazol-1-yl)ethylamine hydrochloride

Starting material: 7-tert-Butyl-1H-thieno[2,3-g]indazole

EXAMPLE 58

In the similar manner as described in Reference Example 79, (S)-1-benzyloxycarbonyl-2-(3-methyl-1H-furo[2,3-g]indazol-1-ylmethyl)pyrrolidine was obtained from 3-methyl-1H-furo[2,3-g]indazole and (S)-(1-benzyloxycarbonylpyrrolidin-2-yl)methyl methanesulfonate. This compound was dissolved in ethanol (20 ml), 0.06 g of 10% palladium-carbon was added, followed by stirring at room temperature for 12 hours under an atmosphere of hydrogen gas. The reaction mixture was filtered using celite and the solvent was evaporated under a reduced pressure. The thus obtained residue was dissolved by adding 3 ml of methanol, 5 ml of ether was added, the thus resulting precipitate was collected by filtration, dried under a reduced pressure and dissolved in 5 ml of methanol. Then, 10 ml of 4 N hydrochloric acid ethyl acetate solution was added, the solvent was evaporated, and the resulting residue was dissolved in methanol. Then, ether was added and the resulting precipitate was collected by filtration and dried under a reduced pressure to give 0.17 g of (S)-3-methyl-1-(pyrrolidin-2-ylmethyl)-1H-furo[2,3-g]indazole dihydrochloride.

Compounds of Examples 59 to 62 were obtained in the similar manner as described in Example 58.

EXAMPLE 59

(S)-3-Ethyl-1-(pyrrolidin-2-ylmethyl)-1H-furo[2,3-g]indazole hydrochloride

EXAMPLE 60

1-[(R)-2-Pyrrolidinylmethyl]-1H-furo[2,3-g]indazole dihydrochloride

Starting material: 1H-Furo[2,3-g]indazole and (R)-(1-benzyloxycarbonylpyrrolidin-2-yl)methyl methanesulfonate

EXAMPLE 61

1-[(S)-2-Pyrrolidinylmethyl]-1H-furo[2,3-g]indazole dihydrochloride

Starting material: 1H-Furo[2,3-g]indazole and (S)-(1-benzyloxycarbonylpyrrolidin-2-yl)methyl methanesulfonate

EXAMPLE 62

1-(2-Piperidylmethyl)-1H-furo[2,3-g]indazole hydrochloride

EXAMPLE 63

A 0.04 g of platinum oxide was added to a methanol (10 ml) solution of 0.37 g 1-(2-methyl-2-nitro-1-propyl)-1H-furo[2,3-g]indazole, and the mixture was stirred at room temperature for 24 hours in an atmosphere of hydrogen gas. The reaction mixture was filtered using celite and the solvent was evaporated under a reduced pressure. The thus obtained residue was purified by a silica gel column chromatography (eluent: chloroform/methanol/saturated aqueous ammonia =100/10/1) and then treated with 4 N hydrochloric acid ethyl acetate solution in methanol/ethyl acetate to give 0.14 g of 2-(1H-furo[2,3-g]indazol-1-yl)-1,1-dimethylethylamine dihydrochloride.

EXAMPLE 64

A 0.50 g of 2-(1H-furo[2,3-g]indazol-1-yl)cyclopentanone was dissolved in 10 ml of ethanol, 0.43 g of hydroxylamine hydrochloride and 2 ml of pyridine were added, followed by heating under reflux for 1 hour. After cooling of the reaction mixture, the solvent was evaporated under a reduced pressure and the resulting residue was dissolved in chloroform. This solution was washed with water and saturated sodium chloride aqueous solution and then dried with magnesium sulfate. After removal of the drying agent by filtration, the solvent was concentrated under a reduced pressure and the resulting residue was recrystallized from a mixture of acetic acid and chloroform. From this compound, 2-(1H-furo[2,3-g]indazol-1-yl)cyclopentylamine fumarate having a diastereomer ratio of about 7 to 3 was obtained in the similar manner as described in Example 1.

EXAMPLE 65

2-(1H-Furo[2,3-g]indazol-1-yl)-1-phenylethylamine 0.5 fumarate was obtained in the similar manner as described in Example 64.

EXAMPLE 66

To an ethyl acetate (10 ml) solution containing 0.46 g of 1-(1-t-butoxycarbonylazetidin-3-ylmethyl)-1H-furo[2,3-g]indazole was added 4 N hydrochloric acid ethyl acetate solution (3 ml), and the resulting mixture was stirred at room temperature for 4 hours. After evaporation of the solvent under a reduced pressure, the residue was extracted with chloroform and washed with 1 N sodium hydroxide and then the thus obtained organic layer was dried with anhydrous sodium sulfate. After removal of the drying agent, the solvent was evaporated and the residue was purified by a silica gel column chromatography (eluent: hexane/ethyl acetate =5/1) and then treated with fumaric acid in methanol/ethyl acetate to give 0.19 g of 2-chloromethyl-3-(1H-furo[2,3-g]indazol-1-yl)propylamine fumarate.

Compounds of Examples 67 and 68 were obtained in the similar manner as described in Example 66.

EXAMPLE 67

1-(Azetidin-2-ylmethyl)-(1H-furo[2,3-g]indazole dihydrochloride

Starting material: 1-(1-t-Butoxycarbonylazetidin-2-ylmethyl)-1H-furo[2,3-g]indazole

EXAMPLE 68

1-(Azetidin-3-ylmethyl)-(1H-furo[2,3-g]indazole fumarate

Starting material: 1-(1-t-Butoxycarbonylazetidin-3-ylmethyl)-1H-furo[2,3-g]indazole

EXAMPLE 69

1-(Pyrrolidin-3-yl)-(1H-furo[2,3-g]indazole hydrochloride was obtained through 1-(1-benzoyl-3-pyrrolidinyl)-(1H-furo[2,3-g]indazole from 4-oxo-4,5,6,7-tetrahydrobenzo[b]furan and 3-hydrazino-1-benzoylpyrrolidine in the similar manner as described in Reference Examples 1 and 60 and Example 1.

EXAMPLE 70

2-Chloroethyl chloroformate (0.15 ml) was added to a dichloroethane (20 ml) solution containing 0.17 g of 1-(1-benzylpiperidin-3-ylmethyl)-1H-furo[2,3-g]indazole, and the mixture was heated under reflux for 13 hours. Then methanol (20 ml) was added and the mixture was again heated under reflux for 3 hours. After evaporation of the solvent under a reduced pressure, the residue was dissolved in 1 N hydrochloric acid aqueous solution and washed with ethyl acetate. The thus obtained hydrochloric acid extract was alkalified using potassium carbonate and extracted with chloroform, and the obtained organic layer was dried with anhydrous sodium sulfate. After removal of the drying agent, the solvent was evaporated and the residue was purified by a silica gel column chromatography (eluent: chloroform/methanol/saturated aqueous ammonia 100/10/1) and then treated with 4 N hydrochloric acid ethyl acetate solution in methanol/ethyl acetate to give 0.05 g of 1-(3-piperidylmethyl)-1H-furo[2,3-g]indazole dihydrochloride.

EXAMPLE 71

2-(7-Acetylamino-1H-thieno[2,3-g]indazol-1-yl)ethylamine hydrochloride was obtained in the similar manner as described in Reference Examples 1, 21, 29 and 60 and Example 1.

Chemical structural formulae and physicochemical properties of the compounds obtained in the Reference Example and Examples are shown in the following tables.

Each of the symbols used in the tables means as follows.
Rf.: Reference Example number
Ex.: Example number
NMR: Nuclear magnetic resonance spectrum (DMSO-d6 and TMS internal standard, unless otherwise noted) δ:
m/z: Mass spectrometry data (m/z)
Me: Methyl group
Et: Ethyl group

TABLE 2-1

| Rf. | |
|---|---|
| 1 | NMR: 2.70–2.76(2H, m), 2.90–2.96(2H, m), 3.72–3.78(2H, m), 4.32(2H, t), 4.93(1H, t), 7.30(1H, s), 7.46(1H, d), 7.49(1H, d) |
| 2 | NMR($CDCl_3$): 3.25(1H, t), 3.45(2H, s), 4.06–4.11(2H, m), 4.35–4.38(2H, m), 7.11(1H, d), 7.28(1H, d), 7.42(1H, s) |
| 3 | NMR($CDCl_3$): 2.89–2.95(4H, m), 4.06(2H, t), 4.32(2H, t), 6.58(1H, d), 7.29(1H, s), 7.37(1H, d) |
| 4 | NMR($CDCl_3$): 2.78–2.81(4H, m), 4.05(2H, t), 4.50(2H, t), 6.39(1H, d), 7.30(1H, s), 7.37(1H, d) |
| 5 | NMR($CDCl_3$): 1.29(6H, s), 2.75(2H, s), 4.06(2H, t), 4.32(2H, t), 6.59(1H, d), 7.32(1H, s), 7.38(1H, d) |
| 6 | NMR($CDCl_3$): 3.28(1H, t), 3.59(2H, s), 4.06–4.11(2H, m), 4.39–4.43(2H, m), 7.15(1H, d), 7.34(1H, d), 7.39(1H, s) |
| 7 | NMR($CDCl_3$): 2.77–2.85(2H, m), 2.85–2.93(2H, m), 3.40–3.50(1H, m), 4.05–4.15(2H, m), 4.34–4.40(2H, m), 7.25(1H, s), 7.34(1H, s) |
| 8 | NMR($CDCl_3$): 2.76–2.85(2H, m), 2.90–2.98(2H, m), 3.38–3.53(1H, brs), 4.05–4.15(2H, m), 4.35–4.41(2H, m), 7.34(1H, s), 7.41(1H, s) |
| 9 | NMR($CDCl_3$): 2.78–2.85(2H, m), 2.85–2.93(2H, m), 3.38(1H, t), 4.06–4.15(2H, m), 4.33–4.39(2H, m), 7.12(1H, s), 7.34(1H, s) |
| 10 | NMR($CDCl_3$): 2.77–2.84(4H, m), 3.91(3H, s), 4.04–4.12(2H, m), 4.33–4.40(2H, m), 6.40(1H, s), 7.30(1H, s) |
| 11 | NMR($CDCl_3$): 2.57(3H, s), 2.83–2.89(2H, m), 2.96–3.02(2H, m), 3.51(1H, t), 4.08(2H, q), 4.39(2H, t), 7.37(1H, s) |
| 12 | NMR($CDCl_3$): 2.71(3H, s), 2.87(2H, t), 3.00(2H, t), 4.05(2H, t), 4.75(2H, t), 7.33(1H, s) |
| 13 | NMR($CDCl_3$): 2.84–2.91(2H, m), 2.94–3.01(2H, m), 7.33(1H, m), 7.51(1H, s) |
| 14 | NMR($CDCl_3$): 2.87–2.92(4H, m), 7.31(1H, s), 7.33(1H, s) |
| 15 | NMR($CDCl_3$): 2.49(3H, s), 2.76–2.92(4H, m), 4.08(2H, t), 4.40(2H, t), 6.92(1H, s), 7.31(1H, s) |
| 16 | NMR($CDCl_3$): 1.32(3H, t), 2.79–2.98(6H, m), 7.05(1H, s), 7.32(1H, s) |
| 17 | NMR: 2.29(3H, s), 2.74–2.85(4H, m), 3.65–3.75(2H, m), 4.14–4.20(2H, m), 6.48(1H, s), 7.20(1H, s) |
| 18 | NMR: 2.27(3H, s), 2.77–2.82(4H, m), 6.23(1H, s), 7.40(1H, s), 12.20(1H, brs) |
| 19 | NMR($CDCl_3$): 1.34(6H, d), 2.85–2.99(2H, m), 3.07–3.18(1H, m), 7.06(1H, s), 7.31(1H, s) |
| 20 | NMR: 1.35(3H, t), 2.66–2.77(4H, m), 3.69–3.76(2H, m), 4.13(2H, q), 4.23–4.28(2H, m), 4.90(1H, t), 6.70(1H, s), 7.25(1H, s) |
| 21 | NMR($CDCl_3$): 2.74–(3H, s), 3.59(2H, s), 4.59–4.69(4H, m), 7.21(1H, d), 7.35(1H, d), 7.41(1H, s) |
| 22 | NMR($CDCl_3$): 2.77(3H, s), 3.45(2H, s), 4.54–4.59(2H, m), 4.65–4.69(2H, m), 7.11(1H, d), 7.29(1H, d), 7.44(1H, s) |
| 23 | NMR($CDCl_3$): 2.78(3H, s), 2.88–2.93(4H, m), 4.53(2H, t), 4.64(2H, t), 6.64(1H, d), 7.33(1H, s), 7.38(1H, d) |

TABLE 2-2

| Rf. | |
|---|---|
| 24 | NMR($CDCl_3$): 1.29(6H, s), 2.74–2.76(7H, m), 4.53(2H, t), 4.65(2H, t), 6.66(1H, d), 7.36(1H, s), 7.40(1H, d) |
| 25 | NMR($CDCl_3$): 1.57(3H, d), 2.31(3H, s), 4.68(1H, dd), 4.82(1H, dd), 5.20–5.31(1H, m), 7.20–7.21(1H, m), 7.40(1H, dd), 7.58(1H, d), 7.77(1H, d), 8.09(1H, s) |
| 26 | NMR($CDCl_3$): 0.99(3H, t), 1.47–1.68(2H, m), 1.73–1.93(2H, m), 2.27(3H, s), 4.71(1H, dd), 4.85(1H, dd), 5.13–5.21(1H, m), 7.22(1H, dd), 7.40(1H, dd), 7.58(1H, d), 7.77(1H, d), 8.08(1H, s) |
| 27 | NMR($CDCl_3$): 1.17–1.21(6H, m), 2.15(3H, s) 4.70–4.89(2H, m), 5.06–5.11(1H, m), 7.19(1H, dd), 7.40(1H, dd), 7.58(1H, d), 7.77(1H, d), 8.09(1H, s) |
| 28 | NMR($CDCl_3$): 1.30–2.02(1H, m), 2.07(3H, s), 4.67–4.89(3H, m), 5.03–5.09(1H, m), 7.17(1H, dd), 7.39(1H, dd), 7.58(1H, d), 7.77(1H, d), 8.09(1H, s) |
| 29 | NMR($CDCl_3$): 3.60(2H, s), 3.79(2H, t), 4.42(2H, t), 7.17(1H, d), 7.35(1H, d), 7.42(1H, s) |
| 30 | NMR($CDCl_3$): 3.46(2H, s), 3.80(2H, t), 4.39(2H, t), 7.12(1H, d), 7.28(1H, d), 7.45(1H, s) |
| 31 | NMR($CDCl_3$): 2.9–2.93(4H, m), 3.74(2H, t), 4.36(2H, t), 6.60(1H, d), 7.34(1H, s), 7.38(1H, d) |
| 32 | NMR($CDCl_3$): 1.30(6H, s), 2.76(2H, s), 3.73(2H, t), 4.20(2H, t), 6.62(1H, d), 7.37(1H, s), 7.39(1H, d) |

TABLE 2-2-continued

Rf.

33 NMR(CDCl$_3$): 1.36(3H, d), 4.12–4.23(1H, m), 4.55–4.58(2H, m), 7.10–7.11(1H, m), 7.38–7.41(1H, m), 7.60(1H, d), 7.76(1H, d), 8.09(1H, s)
34 NMR(CDCl$_3$): 1.26–1.35(4H, m), 1.56–1.83(7H, m), 3.87–3.93(1H, m), 4.53–4.73(2H, m), 7.08(1H, dd), 7.37–7.40(1H, m), 7.60(1H, d), 7.75(1H, d), 8.10(1H, s)
35 NMR(CDCl$_3$): 2.78–2.80(4H, m), 4.67(4H, s), 6.40(1H, d), 7.32(1H, s), 7.39(1H, d)
36 NMR(CDCl$_3$): 2.77–2.93(4H, m), 3.77(2H, t), 4.41(2H, t), 7.25(1H, s), 7.38(1H, s)
37 NMR(CDCl$_3$): 2.76–2.85(2H, m), 2.87–2.98(2H, m), 3.78(2H, t), 4.43(2H, t), 7.39(1H, s), 7.41(1H, s)
38 NMR: 2.72–2.78(2H, m), 2.85–2.91(2H, m), 3.67–3.73(2H, m), 4.46–4.50(2H, m), 7.38(1H, s), 7.57(1H, s)
39 NMR(CDCl$_3$): 2.78–2.82(4H, m), 3.76(2H, t), 3.92(3H, s), 4.42(2H, t), 6.41(1H, s), 7.35(1H, s)
40 NMR(CDCl$_3$): 1.10(3H, t), 1.61–1.80(2H, m), 3.91–4.00(1H, m), 4.53–4.67(2H, m), 7.10(1H, dd), 7.39(1H, dd), 7.60(1H, d), 7.75(1H, d), 8.09(1H, s)
41 NMR(CDCl$_3$): 7.43(1H, s), 4.44(2H, t), 4.22(2H, t), 3.03–2.98(2H, m), 2.89–2.84(2H, m), 2.59(3H, s)
42 NMR(CDCl$_3$): 2.70(3H, s), 2.87(2H, t), 3.02(2H, t), 3.74(2H, t), 4.82(2H, t), 7.35(1H, s)
43 NMR(CDCl$_3$): 2.78–2.90(2H, m), 2.94–3.40(2H, m), 3.72–3.82(2H, m), 4.44–4.52(2H, m), 7.18–7.29(2H, m), 7.34(1H, s)
44 NMR: 1.27(3H, d), 4.24–4.32(1H, m), 4.77–4.83(2H, m), 7.61(1H, d), 7.84(1H, d), 8.29(1H, s), 8.90(1H, s)

TABLE 2-3

Rf.

45 NMR: 1.27(3H, d), 2.71(3H, s), 4.22–4.35(1H, m), 4.70–4.83(2H, m), 7.51(1H, d), 7.73(1H, d), 8.25(1H, s)
46 NMR: 1.33(3H, d), 4.10–4.25(1H, m), 4.69–4.88(2H, m), 7.71–7.74(2H, m), 7.91–7.95(1H, m), 8.03–8.08(1H, m), 8.20(1H, s)
47 NMR(CDCl$_3$): 1.39(3H, d), 4.11–4.23(1H, m), 4.61(2H, d), 7.48(1H, d), 7.63(1H, d), 7.74(1H, s), 8.09(1H, s)
48 NMR: 1.33(3H, d), 4.13–4.24(1H, m), 4.70–4.86(2H, m), 7.65–7.71(2H, m), 8.21(1H, s), 8.33(1H, s)
49 NMR(CDCl$_3$): 1.39(3H, d), 4.11–4.22(1H, m), 4.60(2H, d), 7.45(1H, d), 7.60(1H, s), 7.63(1H, d), 8.08(1H, s)
50 NMR(CDCl$_3$): 2.50(3H, s), 2.76–2.92(4H, m), 3.76(2H, t), 4.45(2H, t), 6.92(1H, s), 7.36(1H, s)
51 NMR(CDCl$_3$): 1.35(3H, d), 2.70(3H, d), 4.16(1H, m), 4.65(2H, m), 7.39(1H, s), 7.50(1H, d), 7.56(1H, d), 8.05(1H, s)
52 NMR(CDCl$_3$): 1.35(3H, d), 1.44(3H, t), 3.04(2H, q), 4.13–4.20(1H, m), 4.58–4.75(2H, m), 7.41(1H, s), 7.52(1H, d), 7.57(1H, d), 8.06(1H, s)
53 NMR: 1.31(3H, d), 2.53(3H, s), 4.10–4.18(1H, m), 4.51–4.71(2H, m), 7.03–7.17(1H, m), 7.35(1H, d), 7.57(1H, d), 8.15(1H, s)
54 NMR(CDCl$_3$): 1.35(3H, d), 1.46(6H, d), 3.35–3.39(1H, m), 4.13–4.18(1H, m), 4.68(2H, ddd), 7.42(1H, s), 7.53(1H, d), 7.57(1H, d), 8.05(1H, s)
55 NMR(CDCl$_3$): 1.42(3H, t), 2.78–2.82(4H, m), 3.73–3.78(2H, m), 4.15(2H, q), 4.39–4.43(2H, m), 6.42(1H, s), 7.35(1H, s)
56 NMR(CDCl$_3$): 1.33(3H, d), 1.41(3H, t), 3.02(2H, q), 4.08–4.24(1H, m), 4.48(2H, d), 7.07(1H, dd), 7.34(1H, dd), 7.54(1H, d), 7.72(1H, d)
57 NMR(CDCl$_3$): 1.01(3H, t), 1.32(3H, d), 1.79–1.93(2H, m), 2.97(2H, t), 4.09–4.20(1H, m), 4.48(2H, d), 7.07(1H, dd), 7.34(1H, dd), 7.53(1H, d), 7.72(1H, d)
58 NMR(CDCl$_3$): 1.31(3H, d), 4.10(3H, s), 4.11–4.16(1H, m) 4.28–4.38(3H, m), 7.01(1H, dd), 7.26(1H, dd), 7.50(1H, d), 7.71(1H, d)
59 NMR: 1.50–2.30(8H, m), 4.05–4.18(1H, m), 5.05–5.15(1H, m), 7.42–7.52(2H, m), 7.63–7.72(1H, m), 8.08–8.18(2H, m)
60 NMR(CDCl$_3$): 3.86(2H, t), 4.84(2H, t), 7.59(1H, d), 7.62–7.64(2H, m), 7.76(1H, d), 8.10(1H, s)
61 NMR(CDCl$_3$): 3.88(2H, t), 4.78(2H, t), 7.48(1H, d), 7.63(1H, d), 7.75(1H, s), 8.10(1H, s)
62 NMR(CDCl$_3$): 3.89(2H, t), 4.81(2H, t), 7.52(1H, d), 7.60(1H, d), 7.93(1H, s), 8.10(1H, s)
63 NMR(CDCl$_3$): 8.16(1H, s), 7.82(1H, d), 7.39(1H, d), 4.81(2H, t), 3.91(2H, t), 2.91(3H, s)
64 NMR(CDCl$_3$): 2.91(3H, s), 3.88(2H, t), 5.18(2H, t), 7.55(1H, d), 7.66(1H, d), 8.01(1H, s)
65 NMR: 7.58–7.70(2H, m), 8.02–8.05(1H, m), 8.15(1H, s), 13.57(1H, brs)
66 NMR(CDCl$_3$): 7.50(1H, d), 7.64(1H, s), 7.67(1H, d), 8.16(1H, s)

TABLE 2-4

| Rf. | |
|---|---|
| 67 | NMR(CDCl$_3$): 7.45(1H, dd), 7.62(1H, d), 7.67(1H, d), 8.08(1H, s) |
| 68 | NMR(CDCl$_3$): 2.68(3H, s), 3.84(2H, t), 4.80(2H, t), 7.38(1H, s), 7.50(1H, d), 7.55(1H, d), 8.06(1H, s) |
| 69 | NMR(CDCl$_3$): 2.67(3H, s), 7.28(1H, s), 7.52(1H, d), 7.59(1H, d), 8.14(1H, s) |
| 70 | NMR(CDCl$_3$): 1.43(3H, t), 3.02(2H, q), 7.31(1H, s), 7.53(1H, d), 7.60(1H, d), 8.14(1H, s) |
| 71 | NMR: 2.51(3H, s), 6.76–6.79(1H, m), 7.28–7.34(1H, m), 7.52–7.57(1H, m), 8.07–8.10(1H, m), 13.29(1H, brs) |
| 72 | NMR(CDCl$_3$): 1.44(6H, d), 3.27–3.36(1H, m), 7.33(1H, s), 7.52(1H, d), 7.59(1H, d), 8.15(1H, s) |
| 73 | NMR(CDCl$_3$): 1.52(3H, t), 3.81–3.86(2H, m), 4.29(2H, q), 4.75–4.80(2H, m), 6.80–6.82(1H, m), 7.37–7.41(1H, m), 7.52(1H, d), 8.05(1H, s) |
| 74 | NMR(CDCl$_3$): 1.87(3H, s), 3.79–3.85(2H, m), 4.69–4.73(2H, m), 5.92(1H, brs), 7.24(1H, dd), 7.38(1H, dd), 7.58(1H, d), 7.74(1H, d), 8.06(1H, s) |
| 75 | NMR(CDCl$_3$): 4.03((3H, s), 6.91(1H, s), 7.44(1H, d), 7.55(1H, d), 8.08(1H, d), 13.31–13.40(1H, brs) |
| 76 | NMR(CDCl$_3$): 1.50(9H, s), 7.34(1H, s), 7.54(1H, d), 7.60(1H, d), 8.14(1H, s) |
| 77 | NMR(CDCl$_3$): 1.91(3H, s), 2.89–2.92(4H, m), 3.72(2H, t), 4.34(2H, t), 6.67(1H, d), 7.31(1H, s), 7.37(1H, d) |
| 78 | NMR(CDCl$_3$): 1.91(3H, s), 2.79(4H, t), 3.71–3.76(2H, m), 4.46–4.50(2H, m), 6.23(1H, brs), 6.39(1H, d), 7.30(1H, s), 7.38(1H, d) |
| 79 | NMR(CDCl$_3$): 1.25(3H, t), 4.23(2H, q), 5.33(2H, s), 6.95(1H, dd), 7.40(1H, dd), 7.61(1H, d), 7.73(1H, d), 8.08(1H, s) |
| 80 | NMR(CDCl$_3$): 3.01(1H, t), 4.18–4.23(2H, m), 4.68–4.71(2H, m), 7.11(1H, dd), 7.39(1H, dd), 7.60(1H, d), 7.75(1H, d), 8.06(1H, s) |
| 81 | NMR: 5.67(2H, s), 7.40–7.42(1H, m), 7.46(1H, d), 7.68(1H, d), 8.08–8.10(1H, m), 8.18(1H, s), 9.79(1H, s) |
| 82 | NMR(CDCl$_3$): 1.33(3H, d), 3.30(1H, d), 4.41–4.63(3H, m), 7.11(1H, c), 7.39(1H, d), 7.60(1H, d), 7.75(1H, d), 8.07(1H, s) |
| 83 | NMR: 1.05(3H, d), 4.20–4.33(1H, m), 4.52–4.61(1H, m), 4.63–4.74(1H, m), 4.92(1H, d), 7.56(1H, d), 7.80(1H, d), 8.21(1H, s), 8.87(1H, s) |
| 84 | NMR: 1.03(3H, d), 2.65(3H, s), 4.20–4.30(1H, m), 4.48–4.56(1H, m), 4.60–4.70(1H, m), 4.90(1H, d), 7.46(1H, d), 7.70(1H, d), 8.17(1H, s) |
| 85 | NMR: 1.10(3H, d), 4.03–4.17(1H, m), 4.45–4.56(1H, m), 4.60–4.73(1H, m), 4.99(1H, d), 7.67–7.71(2H, m), 7.88–7.92(1H, m), 8.01–8.05(1H, m), 8.12(1H, s) |
| 86 | NMR(CDCl$_3$): 1.37(3H, d), 4.49–4.67(3H, m), 7.47(1H, dd), 7.64(1H, d), 7.78(1H, d), 8.07(1H, s) |
| 87 | NMR: 1.10(3H, d), 4.03–4.15(1H, m), 4.43–4.54(1H, m), 4.60–4.70(1H, m), 5.00(1H, d), 7.63–7.67(2H, m), 8.12(1H, s), 8.27(1H, s) |
| 88 | NMR(CDCl$_3$): 1.35(3H, d), 4.38–4.63(3H, m), 7.43(1H, d), 7.59–7.64(2H, m), 8.04(1H, s) |

TABLE 2-5

| Rf. | |
|---|---|
| 89 | NMR(CDCl$_3$): 1.35(3H d), 2.69(3H, s), 4.41–4.59(2H, m), 4.68(1H, dd), 7.43(1H, s), 7.50(1H, d), 7.56(1H, d), 8.04(1H, s) |
| 90 | NMR(CDCl$_3$): 1.35(3H, d), 1.43(3H, t), 3.04(2H, q), 4.46–4.60(2H, m), 4.69(2H, dd), 7.45(1H, s), 7.51(1H, d), 7.56(1H, d), 8.05(1H, s) |
| 91 | NMR: 1.08(3H, d), 2.51(3H, s), 3.98–4.20(1H, m) 4.25–4.60(2H, m), 4.93(1H, d), 7.03–7.08(1H, m), 7.28–7.36(1H, m), 7.49–7.56(1H, m), 8.06(1H, m) |
| 92 | NMR(CDCl$_3$): 1.35(3H, d), 1.45(6H, d), 3.41–3.32(1H, m), 4.60–4.47(2H, m), 4.69(1H, dd), 7.45(1H, s), 7.52(1H, d), 7.57(1H, d), 8.04(1H, s) |
| 93 | NMR(CDCl$_3$): 1.29(3H, d), 4.09(3H, s), 4.20–4.43(3H, m), 7.01(1H, dd), 7.27(1H, dd), 7.51(1H, d), 7.70(1H, d) |
| 94 | NMR(CDCl$_3$): 1.33(3H, d), 4.40–4.45(1H, m), 4.47–4.52(1H, m), 4.56–4.64(1H, m), 7.08–7.12(1H, m), 7.36–7.41(1H, m), 7.60(1H, d), 7.73–7.78(1H, m), 8.07(1H, s) |
| 95 | NMR: 4.45–4.56(1H, m), 4.70–4.90(2H, m), 6.68(1H, d), 7.34–7.38(1H, m), 7.44(1H, d), 7.64(1H, d), 8.10–8.15(1H, m), 8.19(1H, s) |
| 96 | NMR: 1.35–2.10(8H, m), 3.88–4.00(1H, m), 4.40–4.55(1H, m), 4.65(1H, d), 7.36–7.41(1H, m), 7.44–7.48(1H, m), 7.61(1H, d), 8.05–8.08(1H, m), 8.11(1H, s) |
| 97 | NMR(CDCl$_3$): 1.29(3H, d), 1.41(3H, t), 3.00(2H, q), 4.32–4.42(2H, m), 4.47–4.55(1H, m), 7.06(1H, dd), 7.33(1H, dd), 7.53(1H, d), 7.72(1H, d) |
| 98 | NMR: 1.32(3H, d), 4.15–4.22(1H, m), 4.60–4.78(2H, m), 7.44–7.48(1H, m), 7.50–7.58(1H, m), 7.67(1H, d), 8.13(1H, s), 8.19(1H, s) |
| 99 | NMR(CDCl$_3$): 1.05(3H, t), 1.54–1.66(2H, m), 3.37(1H, brs), 4.07–4.15(1H, m), 4.46(1H, dd), 4.61(1H, dd), 7.08–7.10(1H, m), 7.37(1H, d), 7.57(1H, d), 7.73(1H, d), 8.04(1H, s) |

TABLE 2-5-continued

| Rf. | |
|---|---|
| 100 | NMR(CDCl$_3$): 0.95(3H, t), 1.38–1.66(4H, m), 3.36(1H, brs), 4.16–4.22(1H, m), 4.45(1H, dd), 4.59(1H, dd), 7.09(1H, dd), 7.37(1H, dd), 7.57(1H, d), 7.72(1H, d), 8.03(1H, s) |
| 101 | NMR(CDCl$_3$): 1.09(3H, t), 1.82–1.93(1H, m), 3.21(1H, d), 3.91–3.96(1H, m), 4.51(1H, dd), 4.69(1H, dd), 7.10(1H, dd), 7.38(1H, dd), 7.60(1H, d), 7.74(1H, d), 8.07(1H, s) |
| 102 | NMR(CDCl$_3$): 1.09–2.03(10H, m), 3.27(1H, d), 3.56–3.63(1H, m), 3.90–3.95(1H, d), 4.48(1H, dd), 4.66(1H, dd), 7.09(1H, dd), 7.36(1H, dd), 7.57(1H, d), 7.72(1H, d), 8.02(1H, s) |
| 103 | NMR(CDCl$_3$): 1.88(3H, s), 3.68–3.74(2H, m), 4.62(2H, t), 5.35–5.47(1H, brm), 6.63(1H, d), 7.02(1H, d), 7.53(1H, d), 7.61(2H, s), 7.78(1H, s) |
| 104 | NMR: 1.94(3H, d), 6.46(1H, q), 7.56(1H, dd), 7.67(1H, dd), 7.74(1H, d), 8.20(1H, d), 8.33(1H, s) |
| 105 | NMR: 6.33(2H, s), 7.16–7.17(1H, m), 7.46(1H, d), 7.59–7.64(2H, m), 7.69(1H, d), 7.71–7.77(1H, m), 8.00–8.02(1H, m), 8.14(2H, m), 8.18(1H, s) |
| 106 | NMR: 1.80–2.60(6H, m), 5.60(1H, t), 7.46(1H, d), 7.51–7.53(1H, m), 7.66(1H, d), 8.09–8.11(1H, m), 8.16(1H, s) |

TABLE 2-6

| Rf. | |
|---|---|
| 107 | NMR(CDCl$_3$): 1.42(3H, t), 3.01(2H, q), 5.41(2H, s), 7.13(1H, d), 7.43(1H, d), 7.57(1H, d), 7.79(1H, d), |
| 108 | NMR(CDCl$_3$): 2.11–2.21(2H, m), 2.96–3.06(4H, m), 5.25(2H, s), 7.28(1H, s), 7.52(1H, s), 7.95(1H, s) |
| 109 | NMR(CDCl$_3$): 1.45(3H, t), 3.06(2H, q), 5.57(2H, s), 7.45(1H, s), 7.56(1H, d), 7.60(1H, d), 8.08(1H, s) |
| 110 | NMR(CDCl$_3$): 1.47(6H, d), 3.34–3.43(1H, m), 5.58(2H, s), 7.45(1H, s), 7.57(1H, d), 7.61(1H, d), 8.08(1H, s) |
| 111 | NMR(CDCl$_3$): 1.68(6H, s), 5.04(2H, s), 7.12(1H, dd), 7.40(1H, d), 7.59(1H, d), 7.76(1H, d), 8.08(1H, s) |
| 112 | NMR(CDCl$_3$): 1.43(9H, s), 3.18–3.28(1H, m), 3.85(2H, dd), 4.04(2H, t), 7.07(1H, dd), 7.38(1H, dd), 7.69(1H, d), 7.76(1H, d), 8.03(1H, s) |
| 113 | NMR(80° C.): 1.26(9H, s), 2.05–2.28(2H, m), 3.74–3.59(2H, m), 4.57–4.63(1H, m), 4.76(1H, dd), 4.89(1H, dd), 7.34(1H, dd), 7.45(1H, dd), 7.62(1H, d), 8.03(1H, d), 8.09(1H, s) |
| 114 | NMR(CDCl$_3$): 1.50–1.65(4H, m), 2.00–2.07(2H, m), 2.40(1H, br), 2.61–2.72(2H, m), 3.40(1H, d), 3.47(1H, d), 4.48(2H, d), 7.05(1H, dd), 7.21–7.29(5H, m), 7.35(1H, dd), 7.57(1H, d), 7.73(1H, d), 8.01(1H, s) |
| 115 | NMR(CDCl$_3$): 6.29(2H, s), 7.51(1H, d), 7.55(1H, dd), 7.76(1H, d), 8.18(1H, s), 8.28(1H, dd), 8.95(1H, dd) |
| 116 | NMR: 7.55(1H, d), 7.82(1H, d), 8.23(1H, s), 8.83(1H, s), 13.85(1H, brs) |
| 117 | NMR: 2.69(3H, s), 7.45(1H, d), 7.71(1H, d), 8.18(1H, s), 13.72(1H, brs) |
| 118 | NMR(CDCl$_3$): 2.05–2.91(2H, m), 2.95–3.02(4H, m), 7.30(1H, s), 7.52(1H, s), 7.96(1H, s) |
| 119 | NMR: 4.01(3H, s), 7.09(1H, d), 7.29(1H, d), 7.45(1H, d), 8.03(1H, d) |
| 120 | NMR(CDCl$_3$): 2.86–2.94(4H, m), 7.18(1H, s), 7.33(1H, s) |
| 121 | NMR(CDCl$_3$): 2.48(3H, s), 2.84–2.97(4H, m), 7.00(1H, s), 7.32(1H, s) |
| 122 | NMR(CDCl$_3$): 2.63(3H, s), 6.98(1H, d), 7.37(1H, d), 7.54(1H, d), 7.71(1H, d) |
| 123 | NMR(CDCl$_3$): 1.03(3H, t), 1.82–1.95(2H, m), 3.00(2H, t), 6.98(1H, dd), 7.36(1H, dd), 7.57(1H, d), 7.70(1H, d) |
| 124 | NMR(CDCl$_3$): 1.45(3H, t), 3.06(2H, q), 6.98(1H, dd), 7.36(1H, dd), 7.57(1H, d), 7.70(1H, d) |
| 125 | NMR: 4.78–4.88(1H, m), 5.02–5.06(1H, m), 5.28–5.43(1H, m), 7.38–7.42(1H, m), 7.50(1H, d), 7.70(1H, d), 8.13–8.16(1H, m), 8.27(1H, s) |

TABLE 3

| Ex. | G | R | A | |
|---|---|---|---|---|
| 11 | O | H | (S)-sec-butyl (Me-CH-CH2-) | MS: 216(FAB, M⁺+1)<br>NMR: 1.12(3H, d), 3.66–3.78(1H, m), 4.74–4.94(2H, m), 7.48 (1H, d), 7.69(1H, d), 7.79–7.83(1H, m), 8.17(1H, d), 8.22 (1H, s), 8.52(3H, brs) |
| 14 | S | MeO | (S)-sec-butyl | MS: 262(FAB, M⁺+1)<br>NMR: 1.03(3H, d), 4.08(3H, d), 4.57–4.65(1H, dd), 4.72–4.79 (1H, dd), 6.47(2H, s), 7.21(1H, s), 7.52(1H, d), 7.57(1H, d), 8.12(1H, s) |
| 20 | S | Br | —CH₂CH₂— | MS: 296(FAB, M⁺+1)<br>NMR: 3.32(2H, t), 4.95(2H, t), 7.72(1H, d), 7.77(1H, d), 8.24 (1H, s), 8.22–8.27(3H, brs), 8.35(1H, s) |
| 29 | S | Me | —CH₂CH₂— | mp: 186–187° C.<br>NMR: 2.67(3H, s), 3.26(2H, t), 4.87(2H, t), 6.50(2H, s), 7.63 (2H, s), 7.84(1H, s), 8.15(1H, s) |
| 30 | S | Me | (S)-sec-butyl | mp: 195–197° C.<br>NMR: 1.07(3H, d), 2.67(3H, s), 3.59–3.68(1H, m), 4.71(1H, dd), 4.88(1H, dd), 6.51(2H, s), 7.63(2H, s), 7.88(1H, s), 8.16(1H, s) |
| 31 | S | Et | (S)-sec-butyl | MS: 260(FAB, M⁺+1)<br>NMR: 1.06(3H, d), 1.36(3H, t), 3.02(2H, q), 3.60–3.65(1H, m), 4.70(1H, dd), 4.87(1H, dd), 6.50(2H, s), 7.63(2H, s), 7.86(1H, s), 8.16(1H, s). |
| 39 | S | I | —CH₂CH₂— | MS: 344(FAB, M⁺+1)<br>NMR: 3.35(2H, t), 4.92(2H, t), 7.70(1H, d), 7.73(1H, d), 8.04 (2H, brs), 8.23(1H, s), 8.35(1H, s) |
| 43 | O | H | —CH₂CH₂— | MS: 202(FAB, M⁺+1)<br>NMR: 3.30–3.35(2H, m), 4.87(2H, t), 7.47–7.49(1H, m), 7.68–7.70(2H, m), 8.17(1H, d), 8.21(1H, s), 8.25(3H, brs) |
| 47 | S | MeO | —CH₂CH₂— | MS: 248(FAB, M⁺+1)<br>NMR: 3.29–3.35(2H, m), 4.11(3H, s), 4.93(2H, t), 7.29(1H, s), 7.54(1H, d), 7.59(1H, d), 8.12(1H, s), 8.20(2H, brs) |
| 53 | S | Et | —CH₂CH₂— | MS: 246(FAB, M⁺+1)<br>NMR: 1.37(3H, t), 3.02(2H, q), 3.25(2H, t), 4.86(2H, t), 6.49 (2H, s), 7.64(2H, s), 7.82(1H, s), 8.15(1H, s) |

TABLE 4-1

| Ex. | |
|---|---|
| 1 | NMR: 3.25–3.27(2H, m), 3.62(2H, s), 4.59(2H, t), 7.43(1H, s), 7.53(1H, d), 7.62(1H, d), 8.24(3H, brs) |
| 2 | NMR: 3.30–3.22(2H, m), 3.46(2H, s), 4.49(2H, t), 7.23(1H, d), 7.48(1H, s), 7.58(1H, d), 8.25(3H, brs) |
| 3 | NMR: 2.81–2.93(4H, m), 3.15–3.24(2H, m), 4.50(2H, t), 7.14(1H, d), 7.35(1H, s), 7.71(1H, d), 8.33(3H, brs) |
| 4 | NMR: 2.74(4H, s), 3.30–3.34(2H, m), 4.53(2H, t), 6.60(1H, d), 7.38(1H, s), 7.74(1H, d), 8.11(3H, brs) |
| 5 | NMR: 1.23(6H, s), 2.75(2H, s), 3.15–3.26(2H, m), 4.52(2H, t), 7.18(1H, d), 7.40(1H, s), 7.71(1H, d), 8.34(3H, brs) |
| 6 | NMR: 2.72–2.78(2H, m), 2.92–3.00(2H, m), 3.20–3.30(2H, m), 4.58(2H, t), 7.40(1H, s), 7.50–7.60(2H, m), 8.20(2H, brs) |
| 7 | NMR: 1.12(3H, d), 3.66–3.78(1H, m), 4.74–4.94(2H, m), 6.44(1H, brs), 7.48(1H, d), 7.69(1H, d), 7.79–7.83(1H, m), 8.17(1H, d), 8.22(1H, s), 8.52(3H, brs) |
| 8 | NMR: 0.87(3H, t), 1.49–1.57(2H, m), 3.57–3.64(1H, m), 4.75–4.91(2H, m), 7.49(1H, d), 7.68–7.71(2H, m), 8.18(1H, d), 8.23(1H, s), 8.33(1H, brs) |

TABLE 4-1-continued

| Ex. | |
|---|---|
| 9 | NMR: 1.00–1.02(4H, m), 1.16–1.30(1H, m), 1.50–1.84(6H, m), 3.52–3.63(1H, m), 4.82–4.85(2H, m), 7.49(1H, d), 7.62–7.63(1H, m), 7.70(1H, d), 8.18(1H, d), 8.24(1H, s), 8.29(3H, brs) |
| 10 | NMR: 3.31–3.37(2H, m), 4.96–5.02(2H, m), 7.73(1H, d), 7.78(1H, d), 7.99(1H, d), 8.18(1H, d), 8.22(1H, s), 8.23(3H, brs) |
| 12 | mp: 182–185° C. |
| 13 | mp: 174–178° C. |
| 15 | mp: 192–195° C. |
| 16 | NMR: 1.61(9H, s), 3.16–3.23(2H, m), 4.87–4.94(2H, m), 7.74(1H, d), 7.75(1H, s), 7.78(1H, d), 7.96–8.15(3H, brs), 8.41(1H, s) |
| 17 | mp: 250–253° C. |
| 18 | NMR: 1.12(3H, d), 3.65–3.80(1H, m), 4.80–4.88(1H, m), 4.93–5.01(1H, m), 7.46–7.51(1H, m), 7.69(1H, d), 7.91–7.93(1H, m), 8.18(1H, d), 8.22(1H, s), 8.74(3H, brs), 9.94(1H, brs) |
| 19 | NMR: 2.71–2.78(2H, m), 2.86–2.92(2H, m), 3.23(2H, t), 4.53(2H, t), 7.40(1H, s), 7.70(1H, s), 8.01–8.14(2H, brs) |
| 21 | NMR: 7.45(1H, s), 4.56(2H, t), 3.37–3.30(2H, m), 2.98(2H, t), 2.80(2H, t), 2.59(3H, s) |
| 22 | NMR: 2.92(3H, s), 3.48(2H, t), 5.11(2H, t), 7.79(2H, s), 8.27(1H, s) |
| 23 | NMR: 1.09(3H, d), 3.74–3.86(1H, m), 4.78–4.86(2H, m), 6.49(2H, s), 7.61(1H, d), 7.84(1H, d), 8.29(1H, s), 8.91(1H, s) |
| 24 | mp: 177–178° C. |
| 25 | NMR: 1.05(3H, d), 3.50–3.70(1H, m), 4.74–4.78(1H, m), 4.80–4.84(1H, m), 6.49(2H, s), 7.68–7.78(2H, m), 7.95(1H, d), 8.14(1H, d), 8.19(1H, s) |
| 26 | NMR: 1.01(3H, d), 3.50(1H, br), 4.60(1H, dd), 4.77(1H, dd), 6.47(1H, s), 7.68(1H, d), 7.74(1H, d), 8.19(1H, s), 8.31(1H, s) |

TABLE 4-2

| Ex. | |
|---|---|
| 27 | NMR: 1.05(3H, d), 3.55–3.67(1H, m), 4.62–4.72(1H, m), 4.80–4.90(1H, m), 6.50(2H, s), 7.69(2H, s), 8.20(1H, s), 8.39(1H, s) |
| 28 | NMR: 1.05(3H, d), 3.50–3.65(1H, m), 4.65(1H, dd), 4.82(1H, dd), 6.50(2H, s), 7.69(1H, d), 7.77(1H, d), 8.21(1H, s), 8.24(1H, s) |
| 32 | NMR: 1.05(3H, d), 2.52(3H, s), 3.54–3.66(1H, m), 4.55–4.63(1H, m), 4.62–4.68(1H, m), 6.51(2H, s), 7.26(1H, s), 7.37(1H, d), 7.57(1H, d), 8.14(1H, s). |
| 33 | mp: 168–169° C. |
| 34 | mp: 222–226° C. |
| 35 | NMR: 1.12(3H, d), 1.34(3H, t), 2.97(2H, q), 3.64–3.74(1H, m), 4.71(1H, dd), 4.82(1H, dd), 7.43(1H, brd), 7.66(1H, d), 7.77–7.79(1H, m), 8.15(1H, d) |
| 36 | NMR: 0.95(3H, t), 1.11(3H, d), 1.73–1.82(2H, m), 2.92(2H, t), 3.62–3.75(1H, m), 4.69(1H, dd), 4.82(1H, dd), 7.43(1H, d), 7.65(1H, d), 7.76(1H, d), 8.15(1H, d) |
| 37 | NMR: 1.13(3H, d), 3.63–3.68(1H, m), 4.04(3H, s), 4.53(1H, dd), 4.63(1H, dd), 6.55(2H, s), 7.36(1H, d), 7.48(1H, d), 7.63(2H, d), 8.13(1H, d) |
| 38 | NMR: 2.69–2.76(2H, m), 2.88–2.94(2H, m), 3.23(2H, t), 4.54(2H, t), 7.40(1H, s), 7.77(1H, s), 8.20(3H, brs) |
| 40 | NMR: 8.34(1H, s), 8.03(1H, d), 7.54(1H, d), 4.94(2H, t), 3.54–3.51(2H, m), 2.92(3H, s) |
| 41 | NMR: 2.68–2.81(4H, m), 3.24(2H, t), 3.94(3H, s), 4.55(2H, t), 6.83(1H, s), 7.36(1H, s), 8.27(3H, brs) |
| 42 | NMR: 2.72–2.78(2H, m), 2.86–2.93(2H, m), 3.21(2H, t), 4.55(2H, t), 7.40(1H, s), 7.68(1H, s), 8.30(3H, brs) |
| 44 | NMR: 3.43–3.49(2H, m), 4.89(2H, t), 7.18(1H, d), 7.44(1H, d), 7.63(1H, d), 8.17(1H, d), 8.24(1H, s), 8.15(3H, brs) |
| 45 | NMR: 0.73(3H, t), 1.16–1.56(4H, m), 3.64–3.68(1H, m), 4.76–4.93(2H, m), 7.49(1H, d), 7.69(1H, d), 7.72–7.73(1H, m), 8.18(1H, d), 8.23(1H, s), 8.40(3H, brs) |
| 46 | NMR: 0.95–0.98(6H, m), 1.82–1.88(1H, m), 3.60–3.62(1H, m), 4.82(2H, d), 7.50(1H, dd), 7.64(1H, dd), 7.70(1H, d), 8.19(1H, d), 8.24(1H, s), 8.28(3H, brs) |
| 48 | NMR: 3.31(2H, t), 4.86(2H, t), 7.72(1H, d), 7.78(1H, d), 8.24(1H, s), 8.30(1H, s), 8.35(2H, brs) |
| 49 | NMR(CDCl$_3$): 1.15–1.45(2H, br), 3.18–3.28(2H, brt), 4.52(2H, t), 6.61(1H, d), 7.11(1H, d), 7.49(1H, d), 7.59–7.62(2H, brs), 7.68(1H, d) |
| 50 | NMR: 1.48(3H, d), 3.30–3.40(1H, m), 3.50–3.61(1H, m), 5.41–5.51(1H, m), 7.47–7.52(1H, m), 7.62–7.64(1H, m), 7.69(1H, d), 8.16(1H, d), 8.24(1H, s), 8.30–8.40(3H, br) |
| 51 | mp: 182–184° C. |
| 52 | NMR: 2.04–2.11(2H, m), 2.90–2.98(4H, m), 3.25–3.30(2H, m), 4.58(2H, t), 7.50(1H, s), 7.55(1H, s), 8.00(1H, s) |

TABLE 4-2-continued

| Ex. | |
|---|---|
| 54 | NMR: 1.41(6H, d), 3.32(2H, t), 3.37–3.42(1H, m), 4.91(2H, t), 6.53(3H, s), 7.65(2H, s), 7.80(1H, s), 8.17(1H, s) |
| 55 | NMR: 1.34(3H, t), 2.96(2H, q), 3.32(2H, br), 4.77(2H, br), 7.43(1H, d), 7.62(1H, br), 7.66(1H, d), 8.15(1H, br) |

TABLE 4-3

| Ex. | |
|---|---|
| 56 | NMR: 3.10–3.20(2H, m), 3.57(2H, t), 4.46(2H, t), 4.66(2H, t), 6.46(2H, s), 6.73(1H, d), 7.52(1H, d), 8.00(1H, s) |
| 57 | mp: 236–240° C. |
| 58 | NMR: 1.71–2.00(4H, m), 2.54(3H, s), 3.14–3.20(1H, m), 3.28–3.33(1H, m), 3.95–4.01(1H, m), 4.85–4.93(2H, m), 7.45(1H, d), 7.63(1H, d), 7.73(1H, m), 8.15(1H, d) |
| 59 | NMR: 1.34(3H, t), 1.71–2.00(4H, m), 2.99(2H, q), 3.16–3.26(1H, m), 3.28–3.38(1H, m), 3.95–4.05(1H, m), 4.90(1H, dd), 4.99(1H, brd), 7.25(1H, d), 7.63(1H, d), 7.73(1H, d), 8.11(1H, d) |
| 60 | NMR: 1.71–2.00(3H, m), 3.15–3.21(1H, m), 3.28–3.31(1H, m), 3.60–4.05(1H, m), 4.94–5.04(2H, m), 7.49(1H, q), 7.69(1H, d), 7.76(1H, q), 8.17(1H, d), 8.23(1H, s) |
| 61 | NMR: 1.71–1.98(3H, m), 3.15–3.19(1H, m), 3.29–3.30(1H, m), 3.98–4.04(1H, m), 4.93–5.03(2H, m), 7.49(1H, d), 7.69(1H, d), 7.74(1H, d), 8.17(1H, d), 8.23(1H, s) |
| 62 | mp: 222–225° C. |
| 63 | mp: 258–260° C. |
| 64 | NMR: 1.68–2.43(6H, m), 3.71–3.78(0.3H, m), 4.02–4.10(0.7H, m), 5.34–5.48(1H, m), 6.45(2H, s), 7.43–7.47(1H, m), 7.57–7.69(2H, m), 8.10–8.14(1H, m), 8.18–8.21(1H, m) |
| 65 | mp: 172–173° C. |
| 66 | mp: 153–155° C. |
| 67 | NMR: 2.39–2.48(2H, m), 3.65–4.06(3H, m), 4.86–5.11(2H, m), 7.49(1H, d), 7.68(1H, d), 7.71(1H, q), 8.18(1H, d), 8.22(1H, d) |
| 68 | mp: 174–176° C. |
| 69 | NMR: 2.34(1H, m), 2.50(1H, m), 3.43–3.47(2H, m), 3.68(1H, m), 3.77(1H, m), 5.87(1H, m), 7.50(1H, d), 7.64(1H, d), 7.69(1H, d), 8.18(1H, d), 8.24(1H, s), 9.40–9.63(2H, brs) |
| 70 | NMR: 1.26–1.29(1H, m), 1.58–1.76(3H, m), 2.41(1H, br), 2.66–2.88(2H, m), 3.10–3.18(2H, m), 4.56–4.59(2H, m), 7.45(1H, d), 7.63(1H, d), 7.67(1H, d), 8.16(1H, d), 8.17(1H, s) |
| 71 | NMR: 2.16(3H, s), 3.47(2H, m), 4.83(2H, m), 7.41(1H, s), 7.59(1H, d), 7.62(1H, d), 8.01(3H, brs), 8.18(1H, s), 11.56(1H, s) |

What is claimed is:

1. A tricyclic pyrrole or pyrazole derivative represented by the following general formula (I)

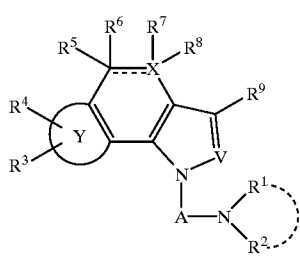

(I)

(each symbol in the above formula means as follows;

Y ring: an unsaturated five-membered ring which may have 1 to 3 of one or more types of hetero atom(s) each selected from the group consisting of a nitrogen atom, an oxygen atom and a sulfur atom or an unsaturated six-membered ring having 1 or 2 nitrogen atom(s), X: a bond or a carbon atom, ═: a double bond or a single bond, V: a nitrogen atom or a group represented by a formula CH, A: a straight or branched lower alkylene group which may be substituted with a halogen atom or a cycloalkyl group, $R^1$ and $R^2$: may be the same or different from each other and each represents a hydrogen atom or a lower alkyl group, or $R^1$ and $R^2$ or A may form a nitrogen-containing saturated heterocyclic ring together with the adjacent nitrogen atom, $R^3$ and $R^4$: may be the same or different from each other and each represents a hydrogen atom, a lower alkyl group, a hydroxyl group, a lower alkoxy group, an amino group, a mono- or di-lower alkylamino group, a lower alkanoylamino group or a halogen atom, and $R^5$ to $R^9$: may be the same or different from one another and each represents a hydrogen atom, a lower alkyl group, a hydroxyl group or a lower alkoxy group, with the proviso that, when ═ is a double bond, then $R^6$ and $R^8$ do not exist and that, when X is a bond, then ═ is a single bond and $R^7$ and $R^8$ do not exist), or a pharmaceutically acceptable salt thereof.

2. The compound according to claim 1, wherein

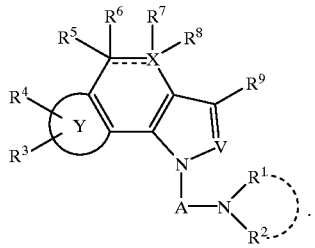

is

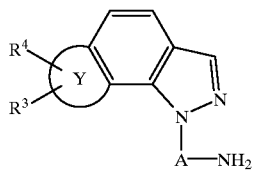

3. The compound according to claim 2, wherein A is ethylene or propylene.

4. The compound according to claim 3, wherein Y ring is a furan ring or a thiophene ring.

5. The compound according to claim 4, wherein it is 2-(1H-furo[2,3-g]indazol-1-yl)ethylamine, 2-(7-bromo-1H-thieno[2,3-g]indazol-1-yl)ethylamine, 2-(7-iodo-1H-thieno[2,3-g]indazol-1-yl)ethylamine, 2-(7-methoxy-1H-thieno[2,3-g]indazol-1-yl)ethylamine, (S)-2-(1H-furo[2,3-g]indazol-1-yl)-1-methylethylamine, 2-(7-methyl-1H-thieno[2,3-g]indazol-1-yl)ethylamine, (S)-2-(7-methoxy-1H-thieno[2,3-g]indazol-1-yl)-1-methylethylamine, (S)-1-methyl-2-(7-methyl-1H-thieno[2,3-g]indazol-1-yl)ethylamine, 2-(7-ethyl-1H-thieno[2,3-g]indazol-1-yl)ethylamine, (S)-2-(7-ethyl-1H-thieno[2,3-g]indazol-1-yl)-1-methylethylamine or a pharmaceutically acceptable salt thereof.

6. A pharmaceutical composition which comprises the compound of claim 1 or a pharmaceutically acceptable salt thereof and a pharmaceutically acceptable carrier.

7. The pharmaceutical composition according to claim 6, which is a 5-$HT_{2C}$ ligand.

8. The pharmaceutical composition according to claim 7, which is a therapeutic drug of impotence.

* * * * *